(12) United States Patent
Bymaster et al.

(10) Patent No.: US 9,566,264 B2
(45) Date of Patent: Feb. 14, 2017

(54) COMBINATIONS AND METHODS

(71) Applicant: Euthymics Bioscience, Inc., Cambridge, MA (US)

(72) Inventors: Frank Bymaster, Brownsburg, IN (US); Anthony McKinney, Cambridge, MA (US)

(73) Assignee: EUTHYMICS BIOSCIENCE, INC., Cambridge, MA (US)

( * ) Notice: Subject to any disclaimer, the term of this patent is extended or adjusted under 35 U.S.C. 154(b) by 0 days.

(21) Appl. No.: 14/321,635

(22) Filed: Jul. 1, 2014

(65) Prior Publication Data
US 2015/0005359 A1 Jan. 1, 2015

Related U.S. Application Data

(60) Provisional application No. 61/841,924, filed on Jul. 1, 2013.

(51) Int. Cl.
*A61K 31/403* (2006.01)
*A61K 31/167* (2006.01)

(52) U.S. Cl.
CPC .......... *A61K 31/403* (2013.01); *A61K 31/167* (2013.01)

(58) Field of Classification Search
None
See application file for complete search history.

(56) References Cited

U.S. PATENT DOCUMENTS

| | | | |
|---|---|---|---|
| 4,122,193 A | 10/1978 | Scherm et al. | |
| 4,131,611 A | 12/1978 | Fanshawe et al. | |
| 4,196,120 A | 4/1980 | Fanshawe et al. | |
| 4,231,935 A | 11/1980 | Fanshawe et al. | |
| 4,435,419 A | 3/1984 | Epstein et al. | |
| 6,132,724 A | 10/2000 | Blum | |
| 6,204,284 B1 | 3/2001 | Beer et al. | |
| 6,372,919 B1 | 4/2002 | Lippa | |
| 6,569,887 B2 | 5/2003 | Lippa et al. | |
| 7,098,229 B2 | 8/2006 | Lippa et al. | |
| 8,765,801 B2 | 7/2014 | Hagen et al. | |
| 9,139,521 B2 | 9/2015 | Hagen et al. | |
| 2006/0019966 A1 | 1/2006 | Deecher et al. | |
| 2006/0020014 A1* | 1/2006 | Abou-Gharbia et al. | .... 514/412 |
| 2006/0020015 A1 | 1/2006 | Abou-Gharbia et al. | |
| 2006/0223875 A1 | 10/2006 | Skolnick et al. | |
| 2007/0043100 A1 | 2/2007 | Hagen | |
| 2009/0326245 A1 | 12/2009 | Hagen | |
| 2011/0294847 A1 | 12/2011 | Hagen | |
| 2012/0258994 A1 | 10/2012 | McKinney et al. | |
| 2014/0039029 A1 | 2/2014 | McKinney et al. | |
| 2014/0228421 A1 | 8/2014 | McKinney et al. | |
| 2014/0315892 A1 | 10/2014 | McKinney et al. | |
| 2016/0008324 A1 | 1/2016 | Hagen et al. | |

FOREIGN PATENT DOCUMENTS

| WO | WO 2006/012474 A1 | 2/2006 |
|---|---|---|
| WO | WO 2006/012476 A2 | 2/2006 |
| WO | WO 2006/012477 A1 | 2/2006 |
| WO | WO 2007/013936 A2 | 2/2007 |

OTHER PUBLICATIONS

Database Registry in STN, entry for compund RN=410074-74-7, entered in database May 2, 2002.*
Abraham et al. Genetic polymorphism of CYP2D6. Indian J Pharmacol. 2001;33:147-69.
Atkinson et al. "Effect of noradrenergic and serotonergic antidepressants on chronic low back pain intensity" PAIN, 1999, 83: 137-145.
Basile et al. "Characterization of the antinociceptive actions of bicifadine in models of acute, persistent, and chronic pain". The Journal of pharmacology and experimental therapeutics, 2007, 321 (3): 1208-1225.
Bernard et al. "Inter-ethnic differences in genetic polymorphisms of CYP2D6 in the U.S. population: clinical implications", Oncologist, 2006, 11:126-35.
Briley, M., "Clinical Experience with dual action antidepressants in different chronic syndromes", Hum. Psychopharmacol. Clin. Exp., 2004, 19:S21-S25, Abstract Only.
Bymaster, F., et al., "Biopharmaceutical Characterization, Metabolism, and Brain Penetration of the Triple Reuptake Inhibitor Amitifadine," Drug Metabolism Letters, 2013, 7:23-33.
Byrne et al. "Loss of antidepressant efficacy during maintenance therapy: possible mechanisms and treatments" J Clin Psychiatry., 1998, 59(6):279-88, Abstract Only.
Cai et al. "CYP2D6 genetic variation in healthy adults and psychiatric African-American subjects: implications for clinical practice and genetic testing" The Pharmacogenomics Journal, 2006, 6, 343-350.

(Continued)

*Primary Examiner* — Brian J Davis
(74) *Attorney, Agent, or Firm* — Hoxie & Associates LLC

(57) ABSTRACT

The present disclosure relates to novel methods of treating pain comprising administering to a human in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the human is a heavy drinker and/or binge drinker and/or wherein the human has compromised liver function and/or wherein the human is a codeine non-responder. The present disclosure also relates to a method of treating pain comprising concurrently or sequentially administering to a patient in need thereof an effective amount of (a) (1R,5S)-(+)-1-(3,4-dichlorophenyl)-3-azabicyclo[3.1.0]hexane, in free and/or pharmaceutically acceptable salt form, and (b) acetaminophen. The present disclosure also relates to a method of treating pain comprising simultaneously or sequentially administering to a patient in need thereof an effective amount of (a) (1R,5S)-(+)-1-(3,4-dichlorophenyl)-3-azabicyclo[3.1.0]hexane, in free and/or pharmaceutically acceptable salt form, and (b) a non-steroidal anti-inflammatory drug.

23 Claims, 8 Drawing Sheets

(56) References Cited

OTHER PUBLICATIONS

Chandler et al. "Validation of the Massachusetts General Hospital Antidepressant Treatment History Questionnaire (ATRQ)", CNS Neurosci Ther., 16:322-325, Sep. 21, 2009. [Epub ahead of print].
Chong et al. "Pharmacogenetics of the Proton Pump Inhibitors: A Systematic Review", Pharmacotherapy, 2003, 23:460-71.
Coric et al. Sheehan Suicidality Tracking Scale (Sheehan-STS) Preliminary Results from a Multicenter Clinical Trial in Generalized Anxiety Disorder. Psychiatry, 2009, 6 (1): 26-31.
Crews et al. "Clinical Pharmacogenetics Implementation Consortium. Clinical Pharmacogenetics Implementation Consortium (CPIC) guidelines for codeine therapy in the context of cytochrome P450 2D6 (CYP2D6) genotype", Clin Pharmacol Ther. Feb. 2012;91(2):321-6.
DeLorenzo et al., "SEP-225289 Serotonin and Dopamine Transporter Occupancy: A PET Study," J Nuc Med, 2011, 52(7): 1150-1155.
DeVane' "Antidepressant—Drug Interactions are Potentially but Rarely Clinically significant" Neuropsychopharmacology 31, 2006, 1594-1604.
Di Chiara et al. "Dopamine and drug addiction: The nucleus accumbens shell connection" Neuropharmacology, 2004, 47 Suppl 1: 227-241.
Eshleman, A. J. et al., Journal of Pharmacology & Experimental Therapeutics, 1999, 289:877-885.
Fava et al. "Definition and epidemiology of treatment-resistant depression", Psychiatr Clin North Am. 1996, 19:179-200.
Fava et al. "The problem of the placebo response in clinical trials for psychiatric disorders: culprits, possible remedies, and a novel study design approach", Psychother Psychosom. 2003;72(3):115-27.
Fava et al. "Reliability and validity of the Massachusetts general hospital cognitive and physical functioning questionnaire", Psychother Psychosom. 2009;78(2):91-7.
Fava et al. "15 years of clinical experience with bupropion HCl: from bupropion to bupropion SR to bupropion XL", Prim Care Companion J Clin Psychiatry. 2005;7(3):106-13.
Fava, "Diagnosis and definition of treatment-resistant depression", Biol Psychiatry. 2003;53(8):649-59.
Fava, "Prospective studies of adverse events related to antidepressant discontinuation", J Clin Psychiatry. 2006;67 Suppl 4:14-21.
Forcehimes et al. "Psychometrics of the Drinker Inventory of Consequences (DrInC)", Addict Behav. Aug;32(8):1699-704 (2007).
Frantz S., Drug discovery: playing dirty. Nature. 2005;437:942-3.
Gu, H., et al. J. Biol. Chem. 269:7124-7130 (1994).
Guengerich FP, "Cytochrome P450 and chemical toxicology". Chem. Res. Toxicol., 2008, 21(1): 70-83.
Hamilton M., "A Rating Scale for Depression", J. Neurol. Neurosurg. Psychiat., 1960, 23, 56.
Hamilton M., "Development of a rating scale for primary depressive illness", Br J Soc Clin Psychol. 1967;6(4):278-96.
Hamilton, "The assessment of anxiety states by rating", British Journal of Medical Psychology, 32, 50-55 (1959).
Hollenberg, "Characteristics and common properties of inhibitors, inducers, and activators of cyp enzymes drug metabolism reviews", 34(1 & 2), 17-35 (2002).
Ingelman-Sundberg M., "Pharmacogenetics of cytochrome P450 and its applications in drug therapy: the past, present and future", Trends Pharmacol Sci.(4):193-200 (2004).
Johansson et al. "Genetic Polymorphism and Toxicology—With Emphasis on Cytochrome P450", Toxicol. Sci. (2011) 120 (1): 1-13.
Judd et al. "Major depressive disorder: a prospective study of residual subthreshold depressive symptoms as predictor of rapid relapse". J Affect Disord. 1998;50(2-3):97-10.
Judd et al. "Does incomplete recovery from first lifetime major depressive episode herald a chronic course of illness?", Am J Psychiatry. 2000;157(9):1501-4.

Keller, "Relapse in major depressive disorder: analysis with the life table", Arch Gen Psychiatry. 1982;39(8):911-5 Abstract Only.
Kung et al., "The Clinical Use of Pharmacogenomic Testing in Treatment-Resistant Depression", Primary Psychiatry, 2010, 14 pages.
Labbate et al. "Sexual dysfunction in male psychiatric outpatients: validity of the Massachusetts General Hospital Sexual Functioning Questionnaire", Psychother Psychosom. 2001;70(4):221-5.
Lobello et al. "Cytochrome P450 2D6 phenotype predicts antidepressant efficacy of venlafaxine: a secondary analysis of 4 studies in major depressive disorder", J Clin Psychiatry. Nov. 2010;71(11):1482-7.
Lynch et al. "The Effect of Cytochrome P450 Metabolism on Drug Response, Interactions, and Adverse Effects", Am Fam Physician. Aug. 1, 2007;76(3):391-396.
L. L. McCoy, J. Am. Chem. Soc., 80, 6568 (1958).
McMillen et al. "Effect of DOV 102,677 on the volitional consumption of ethanol by Myers' high ethanol-preferring rat" Alcoholism, clinical and experimental research, 2007, 31(11): 1866-1871.
Miller et al. "The treatment of chronic depression, part 3: psychosocial functioning before and after treatment with sertraline or imipramine", J Clin Psychiatry. 1998;59(11):608-19.
Montgomery et al. "A new depression scale designed to be sensitive to change", British Journal of Psychiatry 1979;134:382-9.
Mrazek, "Psychiatric pharmacogenomic testing in clinical practice", Dialogues Clin Neurosci. 2010;12(1):69-76.
Meunier, "Mechanism of oxidation reactions catalyzed by cytochrome p450 enzymes", Chem Rev. Sep. 2004;104(9):3947-80.
Nyenhuis et al. "Adult and geriatric normative data and validation of the profile of mood states", J Clin Psychol. Jan. 1999;55(1):79-86.
Olsen et al. The internal and external validity of the Major Depression Inventory in measuring severity of depressive states Psychological Medicine (2003), 33 : 351-356 Cambridge University Press.
Papakostas et al. "Treatment of SSRI-resistant depression: a meta-analysis comparing within—versus across-class switches", Biol Psychiatry. Apr. 1, 2008;63(7):699-704.
Parker et al. "Tolerance to desvenlafaxine in rapid metabolizing depressed patients", Int Clin Psychopharmacol, 2011, 26(2):84-7.
Paykel et al. "Residual symptoms after partial remission: an important outcome in depression", Psychol Med. Nov. 1995;25(6):1171-80.
Perovic et al. Arzneimittelforschung 45: 1145-1148 (1995) Abstract Only.
Polasek et al. Perpetrators of pharmacokinetic drug-drug interactions arising from altered cytochrome P450 activity: a criteria-based assessment', Br J Clin Pharmacol., 2011, 71(5):727-36.
Posner et al.. "Columbia Classification Algorithm of Suicide Assessment (CCASA): Classification of Suicidal Events in the FDA's Pediatric Suicidal Risk Analysis of Antidepressants", Am J Psychiatry, 2007, 164:1035-1043.
Povlock, et al. "Neurotransmitter transporters: structure, function, and regulation," Reith M E A, Editor, Humana Press, Totowa, pp. 1-28 (1997).
Preskorn SH, "Do you feel lucky?", J Prac Psycho Behav Hlth. 1998;4:37-40.
Quitkin et al., "Antidepressant", Chapter 2 in "Current Psychotherapeutic Drugs", Second Edition, 1998, 7 pages.
Roth et al. "Magic shotguns versus magic bullets: selectively non-selective drugs for mood disorders and schizophrenia". Nature reviews. Drug discovery, 2004, 3 (4): 353-359.
Rush et al. "Acute and longer-term outcomes in depressed outpatients requiring one or several treatment steps", Am J Psychiatry. Nov. 2006;163(11):1905-17.
Rush et al. "Bupropion-SR, sertraline, or venlafaxine-XR after failure of SSRIs for depression", N Engl J Med. Mar. 23, 2006;354(12):1231-42.
Sachse et al. "Cytochrome P450 2D6 Variants in a Caucasian Population: Allele Frequencies and Phenotypic Consequences", Am. J. Hum. Genet. 60:284-295, 1997.
Sayette et al. "The measurement of drug craving", Addiction, 2000, 95:S189-S210.

(56) References Cited

OTHER PUBLICATIONS

Schrieber, R., et al., Poster 549.8/X2 ", Pharmacological characterization of the triple monoamine transporter uptake inhibitor SEP225289". Oct. 20, 2009, Abstract.

Scott et al. "Clinical Pharmacogenetics Implementation Consortium. Clinical Pharmacogenetics Implementation Consortium guidelines for cytochrome P450-2C19 (CYP2C19) genotype and clopidogrel therapy", Clin Pharmacol Ther. Aug. 2011;90(2):328-32.

Sheehan et al. "The Mini-International Neuropsychiatric Interview (M.I.N.I.): the development and validation of a structured diagnostic psychiatric interview for DSM-IV and ICD-10", J Clin Psychiatry. 1998; 59 Suppl. 20:22-33; quiz 34-57, Abstract Only.

Skolnick, "Antidepressants beyond monoamine-based therapies: clues to new approaches", J Clin Psychiatry. 2002;63:19-23, Abstract Only.

Skolnick et al. Antidepressant-like actions of DOV 21,947: A triple reuptake inhibitor. European Journal of Pharmacology 2003 461:99-104.

Skolnick, P. et al., ""Broad spectrum" antidepressants: Is more better for the treatment of depression", Life Sci., 2003, 73: 3175-3179.

Skolnick, P., et al., "Preclinical and Clinical Pharmacology of DOV 216,303, a "Triple" Reuptake Inhibitor", CNS Drug Reviews (2006).

Skolnick "Dopamine and glutamate in psychiatric disorders," W. Schmidt, Editor; Humana Press Chapter 9, pp. 199-214, 2005, Abstract Only.

Targum et al. "Redefining affective disorders: relevance for drug development", CNS Neurosci Ther. 2008, Spring;14(1):2-9.

Teh et al., "Pharmacogenetics of 2YPD6: Molecular Genetics, Interethnic Differences and Clinical Importance", Drug Metab. Pharmacokinet. 27 (1): 55-67 (2012).

Thase et al. "Remission rates during treatment with venlafaxine or selective serotonin reuptake inhibitors", Br J Psychiatry. 2001;178:234-41.

Thase et al. "Relapse after cognitive behavior therapy of depression: potential implications for longer courses of treatment", Am J Psychiatry. 1992;149(8):1046-52.

Thase et al. "Evaluating antidepressant therapies: remission as the optimal outcome", J Clin Psychiatry, 2003;64(Suppl 13):18-25.

Tizzano et al. "The triple uptake inhibitor (1R,5S)-(+)-1-(3,4-dichlorophenyl)-3-azabicyclo3.1.0 hexane hydrochloride (DOV 21947) reduces body weight and plasma triglycerides in rodent models of diet-induced obesity", The Journal of pharmacology and experimental therapeutics, 2008. 324 (3): 1111-1126.

Tran et al., "Efficacy and tolerability of the novel triple reuptake inhibitor amitifadine in the treatment of patients with major depressive disorder: A Randomized, double-blind, placebo-controlled trial", Journal of Psychiatric Research, 2012, 46:64-71.

Trivedi et al. "Medication augmentation after the failure of SSRIs for depression", N. Engl J Med. Mar. 23, 2006;354(12):1243-52.

Trivedi et al. "The Inventory of Depressive Symptomatology, Clinician Rating (IDS-C) and Self-Report (IDS-SR), and the Quick Inventory of Depressive Symptomatology, Clinician Rating (QIDS-C) and Self-Report (QIDS-SR) in public sector patients with mood disorders: a psychometric evaluation", Psychol Med 2004;34(1):73-82.

Van der Weide et al. "The Influence of Cytochrome P450 Pharmacogenetics on Disposition of Common Antidepressant and Antipsychotic Medications", Clin Biochem Rev vol. 27 Feb. 2006.

Van Londen et al. "Three- to 5-year prospective follow-up of outcome in major depression", Psychol Med. 1998;28(3):731-5.

Zajecka, "Treating depression to remission" J Clin Psychiatry., 2003;64(Suppl 15):7-12.

Žourková et al. "Paroxetine-Induced Conversion of Cytochrome P450 2D6 Phenotype and Occurence of Adverse Effects", Gen. Physiol. Biophys., 2003, 22, 103-113.

U.S. Appl. No. 13/964,024, McKinney et al., filed Aug. 9, 2013.

"Clinical Global Impression (CGI)," 2 pages, [online] [Retrieved Sep. 20, 2016] Retrieved from the Internet. <URL: http://www.psywellness.com.sg/docs/CGI.pdf>.

"Depression," World Health Organization, 2 pages, [online] [Retrieved Jan. 1, 2015] Retrieved from the Internet: <URL: http://www.who.int/mental_health/management/depression/definition/en/>.

Preskorn, S., "Clinical Pharmacology of SSRI's, 7—Why are CYP Enzymes Important When Prescribing SSRIs?," 11 pages, [online] [Retrieved Jan. 5, 2015] Retrieved from the Internet: <URL: http://www.preskorn.com/books/ssri_s7.html>.

"Sepracor Provides Update on Clinical Trials for SEP-225289 and LUNESTA® Pediatrics," dated 2009, 3 pages, [online] [Retrieved Jan. 5, 2015] Retrieved from the Internet: <URL: http://www.fiercebiotech.com/press-releases/sepracor-provides-update-clinical-trials-sep-225289-and-lunesta-r-pediatrics>.

\* cited by examiner

COMBINATIONS AND METHODS

CROSS-REFERENCE TO RELATED APPLICATIONS

This application claims the benefit of U.S. Provisional Application No. 61/841,924, filed on Jul. 1, 2013, the contents of which are hereby incorporated by reference.

TECHNICAL FIELD

The present disclosure relates to novel methods of treating pain comprising administering to a human in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the human is a heavy drinker and/or binge drinker and/or wherein the human has compromised liver function and/or wherein the human is a codeine non-responder. The present disclosure also relates to a method of treating pain comprising concurrently or sequentially administering to a patient in need thereof an effective amount of (a) (1R,5S)-(+)-1-(3,4-dichlorophenyl)-3-azabicyclo[3.1.0]hexane, in free and/or pharmaceutically acceptable salt form, and (b) acetaminophen. The present disclosure also relates to a method of treating pain comprising concurrently or sequentially administering to a patient in need thereof an effective amount of (a) (1R,5S)-(+)-1-(3,4-dichlorophenyl)-3-azabicyclo[3.1.0]hexane, in free and/or pharmaceutically acceptable salt form, and (b) a non-steroidal anti-inflammatory drug.

BACKGROUND

Pain is a sensory experience distinct from sensations of touch, pressure, heat and cold. It is often described by sufferers in such terms as bright, dull, aching, pricking, cutting or burning and is generally considered to include both the original sensation and the reaction to that sensation. It can be classified by the duration as either acute or chronic, or by the cause as either nociceptive, in that it is being caused by the ongoing activation of pain receptors or neuropathic in that it is caused by changes in the nervous system.

Nociceptive pain, also called acute pain, is caused by activation of the nocioceptors, sensory neurons that respond to stimuli which can cause tissue damage such as sprains, bone fractures, burns, bumps, bruises, or inflammation. Nociceptive pain usually resolves once the condition that precipitated it is healed and is generally responsive to opioids and traditional analgesics.

Neuropathic pain syndromes are linked by injury or damage to either the peripheral and/or the central nervous system. The symptoms associated with neuropathic pain conditions include allodynia (painful response to a non-noxious stimulus, such as the touch of clothing), hyperalgesia (heightened or extreme sensitivity to painful stimuli), paraesthesias (abnormal sensations such as tingling, burning, pricking or tickling), hyperesthesia (enhanced sensitivity to a natural stimuli), and dysesthesias (disagreeable sensations produced by ordinary stimuli). Neuropathic pain is generally nonresponsive or only partially responsive to conventional analgesic regimens, such as non-steroidal anti-inflammatory agents, (e.g., ibuprofen; acetaminophen; aspirin; celecoxib) and opioids. Therapeutic methods currently used to treat neuropathic pain include neurosurgery treatments such as nerve block and epidural spinal cord electric stimulus, tricyclic antidepressants (e.g., amitriptyline), intrathecal administration of baclofen, anti-epileptics, milnacipran, duloxetine, pregabalin, and gabapentin.

Pain can be acute, lasting less than thirty days or chronic, lasting more than six months. One in five people suffer from moderate to severe chronic pain, and one in three people are unable or less able to maintain an independent lifestyle due to their pain. It has been reported that between one-half and two-thirds of people with chronic pain are less able or unable to exercise, enjoy normal sleep, perform household chores, attend social activities, drive a car, walk or have sexual relations.

1-(3,4-dichlorophenyl)-3-azabicyclo[3.1.0]hexane was previously described in U.S. Pat. Nos. 4,131,611, 4,196,120, 4,231,935, and 4,435,419.

(1R,5S)-(+)-1-(3,4-dichlorophenyl)-3-azabicyclo[3.1.0] hexane of Formula I, below,

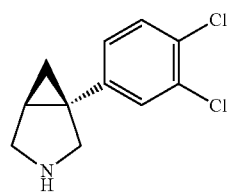

Formula I is a stereoisomer of 1-(3,4-dichlorophenyl)-3-azabicyclo [3.1.0]hexane. (1R,5S)-(+)-1-(3,4-dichlorophenyl)-3-azabicyclo[3.1.0]hexane is described as an anti-depressant in U.S. Pat. No. 7,098,229.

Administration of a racemic, i.e., 50:50, mixture of the (+)- and the (−)-enantiomer of any drug, for example (±)-1-(3,4-dichlorophenyl)-3-azabicyclo[3.1.0]hexane, to a patient can be disadvantageous. First, the racemic mixture might be less pharmacologically active than one of its enantiomers, rendering racemic drugs inherently inefficient. Second, the racemic mixture may be more toxic to a patient than one of its enantiomers, so that administration of a racemic mixture can lead to undesirable side effects in a patient.

Many metabolic routes of elimination may be inhibited or induced by concomitant drug treatment. Metabolic drug-drug interactions (DDIs) may cause substantial changes—an order of magnitude or more decrease or increase in the blood and tissue concentrations of a drug or metabolite—and may affect the extent to which toxic or active metabolites are formed. These large changes in exposure may alter the safety and efficacy profile of a drug and its active metabolites. The risk of DDIs is large because it has been reported that 20.8% of people in the U.S. use three or more drugs per month and 10.2% use 5 or more drugs per month. Serious adverse events may be attributable to DDIs. Cytochrome P450 (CYPs) enzyme isoforms, which catalyze oxidative reactions, account for the metabolism of 75% of all drugs, and in particular, about 80% of drugs cleared by CYPs are metabolized by four CYP isoforms—CYP3A4, CYP2D6, CYP2C9 and CYP2C19. Thus, these four CYPs are potential candidates for DDIs. In addition, CYP2D6 and CYP2C19 are polymorphic and have fast metabolizing and slow metabolizing alleles, which may alter the rate of drug metabolism and plasma drug levels. Physicians must routinely consider potential DDIs and metabolic pathway(s) when selecting treatments.

Few agents and combinations of agents currently prescribed for the treatment of neuropathic pain are fully effective. Additionally, the agents and combinations of agents currently prescribed for chronic pain have limited therapeutic value, losing their efficacy with extended use, and frequently have undesirable side effects including, for example, cognitive changes, sedation, nausea, liver damage, and, in the case of narcotic drugs, respiratory depression, constipation, and addiction. Further, the agents and combinations of agents currently prescribed for chronic pain may be contraindicated in certain patient populations. For instance, as with other opiate-based painkillers, chronic use of codeine can cause physical dependence. In addition, central to the therapeutic action of codeine is its conversion by the cytochrome P-450 metabolizing enzyme 2D6 (CYP2D6) to morphine. Up to 10% of the Caucasian population, however, may have a polymorphism in the metabolizing enzyme that results in the inability to convert codeine to morphine, thus not gaining any analgesia from codeine. Such patients are known as codeine non-responders. Conversely, some people, known as ultrarapid metabolizers, achieve higher-than-expected serum levels of morphine which can lead to side effects such as abdominal pain. In patients treated with duloxetine (Cymbalta®), a serotonin-norepinephrine reuptake inhibitor (SNRI) that is mainly eliminated through hepatic metabolism, there have been reports of hepatic failure, sometimes fatal, and duloxetine should ordinarily not be used in patients with hepatic insufficiency. Elimination of acetaminophen is principally by liver metabolism (conjugation) and subsequent renal excretion of metabolites. Acetaminophen may cause serious liver damage if higher doses are used or if the acetaminophen metabolizing capacity of the liver is overwhelmed as with acetaminophen co-administration with ethanol or when fasting.

Some common analgesics are known to be substrates and/or inducers and/or inhibitors of cytochrome P450 isoforms. Patients taking these analgesics may be at a greater risk of experiencing adverse drug-drug interactions. Analgesics that may pose a risk of drug-drug interactions include, e.g., acetaminophen (CYP1A2 and CYP2E1 substrate), naproxen (CYP1A2 and CYP2C9 substrate), indomethacin (CYP2C19 substrate and inhibitor), diclofenac (CYP2C9 substrate), and celecoxib (CYP2C9 substrate and CYP2D6 inhibitor). CYP inhibitors and inducers that could adversely interact with these analgesics include ciprofloxacin, cimetidine, and fluvoxamine (CYP1A2 inhibitors); amiodarone, fluconazole, fluvastatin, isoniazid, lovastatin, paroxetine, sertraline, zafirlukast, and metronidazole (CYP2C9 inhibitors); bupropion, fluoxetine, paroxetine, quinidine, duloxetine, sertraline, cimetidine, chlorpromazine, diphenhydramine, and ranitidine (CYP2D6 inhibitors); omeprazole and insulin (CYP1A2 inducers); phenobarbital and carbamazepine (CYP2C9 inducers); dexamethasone (CYP 2D6 inducer); and rifampin (CYP1A2, CYP2C9 and CYP2D6 inducer).

Amitriptyline, which may be used to treat neuropathic pain, is a CYP1A2 and CYP2D6 substrate, and can adversely interact with monoamine oxidase inhibitors, anticholinergics, antipsychotics, cimetidine, dilsulfiram, and serotonergic agents (e.g., SSRIs, such as fluoxetine, sertraline, paroxetine and escitalopram).

Further, while it has been reported that as many as 28% of people experiencing chronic pain turn to alcohol to alleviate their suffering, using common analgesics with alcohol may place people at risk for a number of harmful health consequences. For instance, mixing alcohol and acetaminophen may cause acute liver failure and the prescribing information for duloxetine indicates that duloxetine should not be prescribed to patients with substantial alcohol use because duloxetine and alcohol may interact to cause liver injury.

Medications that include combinations of agents for chronic pain may include the undesirable side effects of each agent. For instance, in 2011, the FDA required a boxed warning that highlights the potential for severe injury on all prescription acetaminophen products. Prescription acetaminophen products include acetaminophen with other active ingredients. Acetaminophen with codeine also includes a warning that codeine can produce drug dependence of the morphine type and, therefore, has the potential for being abused.

BRIEF SUMMARY

Provided herein is a method of treating pain comprising administering to a human in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the human is a heavy drinker and/or binge drinker.

Also provided herein is a method of treating pain comprising administering to a patient in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the patient has compromised liver function.

Also provided herein is a method of treating pain comprising administering to a patient in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the patient is a codeine non-responder.

Also provided herein is a method of treating pain comprising concurrently or sequentially administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) acetaminophen.

Also provided herein is a method of treating pain comprising concurrently or sequentially administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) a non-steroidal anti-inflammatory drug.

Also provided herein is a compound of formula

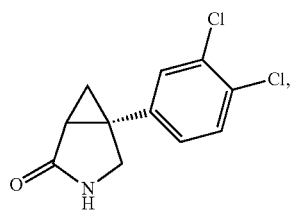 [SMILES: O=C1NC[C@]2(c3ccc(Cl)c(Cl)c3)CC12]

in free or pharmaceutically acceptable salt form.

Also provided herein is a compound of formula

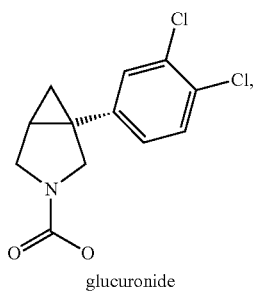

glucuronide in free or pharmaceutically acceptable salt form.

Further areas of applicability of the present disclosure will become apparent from the detailed description provided hereinafter. It should be understood that the detailed description and specific examples, while indicating the preferred embodiments of this disclosure, are intended for purposes of illustration only and are not intended to limit the scope of the disclosure.

DETAILED DESCRIPTION

Figure 1:
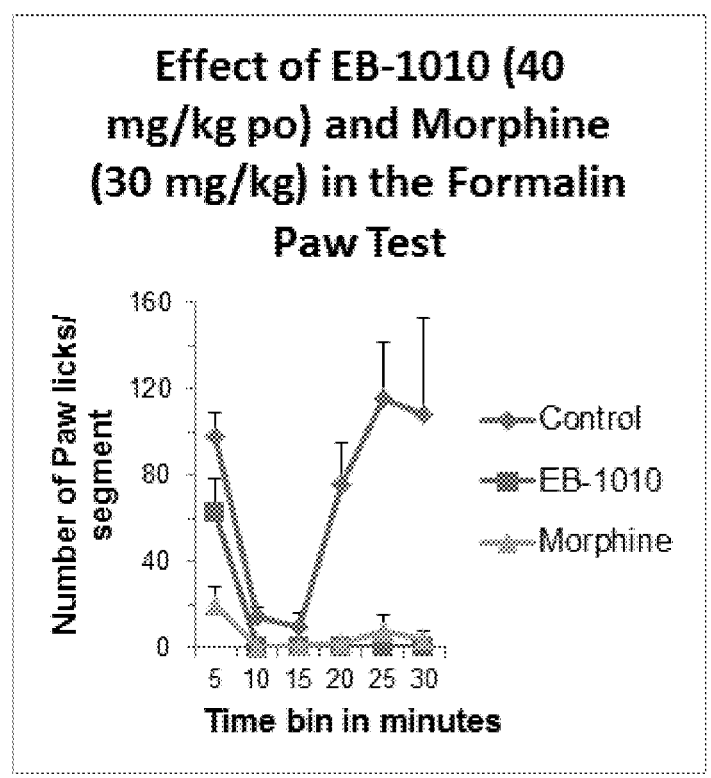
FIG. 1 is a chart illustrating that (1R,5S)-(+)-1-(3,4-dichlorophenyl)-3-azabicyclo[3.1.0]hexane hydrochloride is as effective as morphine in the second phase (15-30 minutes) of the mouse formalin paw lick test model of persistent pain.

The following description of the preferred embodiments is merely exemplary in nature and is in no way intended to limit this disclosure, its application, or uses.

The inventors have discovered that (1R,5S)-(+)-1-(3,4-dichlorophenyl)-3-azabicyclo[3.1.0]hexane has a low affinity for major drug metabolizing CYP enzymes and is metabolized by multiple pathways which may reduce pharmacokinetic drug-drug interactions and effects of enzyme polymorphisms.

Accordingly, provided herein is a method of treating pain comprising administering to a human in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the human is a heavy drinker and/or binge drinker. In some embodiments, the human is a heavy drinker. In some embodiments, the human is a binge drinker. In some embodiments, the human is a heavy drinker and a binge drinker.

Also provided herein is a method of treating pain comprising administering to a patient in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the patient has compromised liver function.

Also provided herein is a method of treating pain comprising administering to a patient in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the patient is a codeine non-responder.

Also provided herein is a method of treating pain comprising concurrently or sequentially administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) acetaminophen.

Also provided herein is a method of treating pain comprising concurrently or sequentially administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) a non-steroidal anti-inflammatory drug.

(1R,5S)-(+)-1-(3,4-dichlorophenyl)-3-azabicyclo[3.1.0]hexane is shown below.

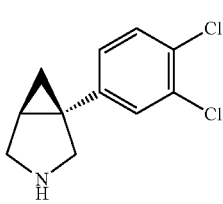

Formula I (1R,5S)-(+)-1-(3,4-dichlorophenyl)-3-azabicyclo[3.1.0]hexane (1R,5S)-(+)-1-(3,4-dichlorophenyl)-3-azabicyclo[3.1.0]hexane is a triple reuptake inhibitor with the greatest potency towards serotonin reuptake (5-HT), half as much towards norepinephrine reuptake (NE), and one eighth as much towards dopamine reuptake (DA).

(1R,5S)-(+)-1-(3,4-dichlorophenyl)-3-azabicyclo[3.1.0] hexane may be synthesized as described in U.S. patent application Ser. No. 11/740,667, incorporated herein by reference in its entirety. Additional exemplary means of preparing (1R,5S)-(+)-1-(3,4-dichlorophenyl)-3-azabicyclo [3.1.0]hexane may be found, for example, in U.S. Provisional Application No. 60/651,505 and U.S. patent application Ser. Nos. 10/466,457, 11/205,956, 12/208,284, and 12/428,399, International Publication Nos. WO2007/127396, WO02/066427, and WO2006/023659, and U.S. Pat. No. 6,372,919, each of which is incorporated herein by reference in its entirety.

As used herein, "(1R,5S)-(+)-1-(3,4-dichlorophenyl)-3-azabicyclo[3.1.0]hexane, in free or pharmaceutically acceptable salt form, substantially free of the corresponding (−) enantiomer" means containing no more than 5% w/w (weight/weight) of the corresponding (−) enantiomer, in free or pharmaceutically acceptable salt form, preferably no more than 2% w/w of the corresponding (−) enantiomer, in free or pharmaceutically acceptable salt form, and more preferably no more than 1% w/w of the corresponding (−) enantiomer.

As used herein, "(1R,5S)-(+)-1-(3,4-dichlorophenyl)-3-azabicyclo[3.1.0]hexane" is to be understood as embracing the compound in any form, for example, free or pharmaceutically acceptable salt form, e.g., as a pharmaceutically acceptable acid addition salt. Pharmaceutically acceptable salts are known in the art and include salts that are physiologically acceptable at the dosage amount and form to be administered, for example, hydrochloride salts.

As used herein, "(1R,5S)-(+)-1-(3,4-dichlorophenyl)-3-azabicyclo[3.1.0]hexane" is also to be understood as embracing the compound in crystalline and amorphous form including, for example, polymorphs, solvates (including hydrates), unsolvated polymorphs (including anhydrates), conformational polymorphs, and amorphous forms of the compounds, as well as mixtures thereof "Crystalline form" and "polymorph" may be used interchangeably herein, and are meant to include all crystalline forms of (1R,5S)-(+)-1-(3,4-dichlorophenyl)-3-azabicyclo[3.1.0]hexane, in free or pharmaceutically acceptable salt form, including, for example, polymorphs, solvates (including hydrates), unsolvated polymorphs (including anhydrates), and conformational polymorphs, as well as mixtures thereof, unless a particular crystalline form is referred to.

(1R,5S)-(+)-1-(3,4-dichlorophenyl)-3-azabicyclo[3.1.0] hexane exists in at least three polymorphic forms, labeled polymorphs A, B, and C, as disclosed in U.S. patent application Ser. Nos. 11/205,956, 12/208,284 and 12/428,399, incorporated herein by reference in their entirety. Crystalline and amorphous forms of (1R,5S)-(+)-1-(3,4-dichlorophenyl)-3-azabicyclo[3.1.0]hexane may be used in any combination or in forms that are substantially free of one or more of the other crystalline forms or free of the amorphous form.

As used herein, "substantially free of other polymorphic forms" means that the crystalline material contains no more than 5% w/w of any other crystalline form.

(1R,5S)-(+)-1-(3,4-dichlorophenyl)-3-azabicyclo[3.1.0] hexane may in some cases also exist in prodrug form. Prodrugs are considered to be any covalently bonded carriers that release the active parent drug in vivo.

As used herein, the words "treatment" and "treating" are to be understood accordingly as embracing prophylaxis and treatment or amelioration of symptoms of disease as well as treatment of the cause of the disease. In one embodiment, this disclosure provides a method for the treatment of the disease or disorder disclosed herein. In another embodiment, this disclosure provides a method for the prophylaxis of a disease or disorder as disclosed herein.

As used herein, "effective amount" is intended to encompass a therapeutically effective amount to treat a specific disease or disorder. A "therapeutically effective amount" means an amount that is capable of providing a therapeutic effect. The specific dose of substance administered to obtain therapeutic effect will, of course, be determined by the particular circumstances surrounding the case, including, for example, the specific substance administered, the route of administration, the condition being treated, and the individual being treated.

As used herein, "heavy drinker" refers to a human male who consumes an average of more than 2 drinks per day or a human female who consumes an average of more than 1 drink per day. A drink comprises about 14 grams of pure alcohol, which may be found in 12 ounces of beer, 8-9 ounces of malt liquor, 5 ounces of wine, and 1.5 ounces of 80 proof spirits (e.g., whiskey, gin, rum, vodka, tequila).

As used herein, "binge drinker" refers to a human male who consumes five or more drinks on one occasion or a human female who consumes four or more drinks on one occasion, at least once in a two week period. A drink comprises about 14 grams of pure alcohol, which may be found in 12 ounces of beer, 8-9 ounces of malt liquor, 5 ounces of wine, and 1.5 ounces of 80 proof spirits (e.g., whiskey, gin, rum, vodka, tequila).

As used herein, a patient with "compromised liver function" refers to a patient who displays abnormal test results for any one of the commonly used liver function tests (e.g., prothrombin time, partial thromboplastin time, serum albumin, serum bilirubin, serum aspartate transaminase, serum alanine transaminase, serum alkaline phosphatase, serum coagulation factor assays, serum glucose, serum lactate dehydrogenase, or platelet count) or who shows signs or symptoms indicating liver damage (e.g., hypocholesterolemia, hypercholesterolemia, malabsorption of fats, hypoglycemia, jaundice). Patients who have compromised liver function may include those suffering from viral hepatitis (acute or chronic), alcoholic hepatitis, autoimmune hepatitis, alcoholic liver disease, drug-induced hepatotoxicity, fatty liver disease, cirrhosis, primary liver cancer (e.g., hepatocellular carcinoma, cholangiocarcinoma, angiosarcoma, hemangiosarcoma), centrilobular necrosis of the liver, end-stage liver disease (including hepatic failure and hepatorenal syndrome), Budd-Chiari syndrome, hemochromatosis, Wilson's disease, Crigler-Najjar syndrome, Dubin-Johnson syndrome, Rotor's syndrome, alpha-1-antitrypsin deficiency, glycogen storage disease, and Gilbert's syndrome.

As used herein, "codeine non-responder" refers to a patient (e.g., human) with a polymorphism that results in the inability to convert codeine to morphine, thus not gaining any analgesia from codeine.

As used herein, "concurrently" means the compounds are administered simultaneously or within the same composition. In some embodiments, the compounds are administered simultaneously. In some embodiments, the compounds are administered within the same composition.

As used herein, the term "patient" includes human or non-human (i.e., animal) patient. In one embodiment, this disclosure encompasses both human and nonhuman. In another embodiment, this disclosure encompasses nonhuman. In other embodiments, the term encompasses human.

As used herein, the term "acute pain" refers to either an initial phase of a painful condition that either largely resolves within several hours, days or months (typically lasting no more than 3 months) or progresses on to a subacute pain (e.g., lasting 3-6 months) or chronic pain (e.g., persisting, in some cases intermittently, for more than 3 months, and often more than 6 months). Acute pain also refers to a transient exacerbation or flare up of a chronic pain condition in which pain intensity worsens substantially, whereby supplemental treatment and/or upwards dose adjustment is indicated, provided that such treatment would be tolerated adequately. Exemplary types of acute pain conditions and symptoms that may be treated or prevented using the methods and compositions of the present disclosure include, but are not limited to, those associated with trauma and other injuries, for example burns; cuts; wounds; trauma; surgery; headaches; sprains; bone fractures; fibromyalgia; acute lower back pain; dorsopathy; dysmenorrhea; infection; dysfunction of the liver, pancreas, endocrine glands, kidney, bladder, gall bladder, spleen, hematopoetic system, vasculature or other body organ or tissue; torn or injured muscle, ligament, or tendon; acute exacerbation of a chronic or intermittent pain condition, including arthritic flare, migraine attack, and acute worsening of chronic lower back pain or chronic neuropathic pain.

As used herein, the term "chronic pain" refers to pain that lasts more than 6 months and/or extends beyond the expected period of healing. Exemplary types of chronic pain conditions and symptoms that may be treated or prevented using the compositions and methods of the present disclosure include, for example, neuropathies, shingles pain, osteoarthritis pain, rheumatoid arthritis pain, cancer pain, and various other chronic pain conditions of non-neuropathic origin, including chronic musculoskeletal pain (for example, chronic low back pain and chronic pain due to osteoarthritis), chronic lumbar and cervical pain, chronic fibromyalgia pain, chronic pain from arteriovenous malformation, arachnoiditis, chronic pain from root avulsion, chronic postthoracotomy pain, and chronic postmastectomy pain of non-neuropathic origin.

As used herein, "neuropathic pain" refers to pain caused by injury or damage to either the peripheral and/or the central nervous system. Exemplary sources of neuropathic pain and related symptoms that may be treated or prevented using the compositions and methods of the present disclosure include, but are not limited to, pain associated with diabetic neuropathy (for example, diabetic peripheral neuropathy), distal symmetrical polyneuropathy, peripheral neuropathy, post-herpetic neuralgia, trigeminal neuralgia, alcoholism-related neuropathy, HIV sensory neuropathy, sciatica, spinal cord injury, post-stroke neuropathy, multiple sclerosis, Parkinson's disease, idiopathic or post-traumatic neuropathy, mononeuritis, cancer-associated neuropathy, peripheral nerve trauma, nerve transection, carpal tunnel injury, neuropathy associated with Fabry's disease, vasculitic neuropathy, neuropathy associated with Guillain-Barre syndrome, entrapment neuropathy, phantom limb syndrome, and various additional neuropathic conditions that may be associated with, for example, fibromyalgia, Wallenberg's syndrome, connective tissue disease, plexus irradiation, ischemic irradiation, hematomyelia, dyscraphism, tumor compression, arteriovenuous malformation, syphilitic myelitis, commissural myelotomy, arachnoiditis, root avulsion, certain chronic lower back pain syndromes of neuropathic origin, and reflex sympathetic dystrophy.

Pain may affect all aspects of life, leading to problems with general activity, walking, work, relations with other people, mood, sleep, and enjoyment of life. Pain may also affect functionality, leading to decreased ranges of motion, decreased strength, decreased activity levels, decreased work levels, and decreased social interactions. The compositions and methods provided herein may be used to increase or normalize one or more of these functional limitations and/or disability caused by pain or conditions or symptoms related to pain.

Provided herein is a method (Method 1) of treating pain comprising administering to a human in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the human is a heavy drinker and/or binge drinker.

1.1 Method 1 wherein the effective amount of (1R,5S)-(+)-1-(3,4-dichlorophenyl)-3-azabicyclo[3.1.0]hexane, in free and/or pharmaceutically acceptable salt form, comprises less than or equal to 2% w/w of the corresponding (−) enantiomer.

1.2 Method 1 or 1.1 wherein the effective amount of (1R,5S)-(+)-1-(3,4-dichlorophenyl)-3-azabicyclo[3.1.0]hexane, in free and/or pharmaceutically acceptable salt form, comprises less than or equal to 1% w/w of the corresponding (−) enantiomer.

1.3 Any of Method 1 et seq. wherein (1R,5S)-(+)-1-(3,4-dichlorophenyl)-3-azabicyclo[3.1.0]hexane is in pharmaceutically acceptable salt form.

1.4 Any of Method 1 et seq. wherein (1R,5S)-(+)-1-(3,4-dichlorophenyl)-3-azabicyclo[3.1.0]hexane in pharmaceutically acceptable salt form is an acid addition salt.

1.5 Any of Method 1 et seq. wherein (1R,5S)-(+)-1-(3,4-dichlorophenyl)-3-azabicyclo[3.1.0]hexane in pharmaceutically acceptable salt form is (1R,5S)-(+)-1-(3,4-dichlorophenyl)-3-azabicyclo[3.1.0]hexane hydrochloride.

1.6 Any of Method 1 et seq. wherein (1R,5S)-(+)-1-(3,4-dichlorophenyl)-3-azabicyclo[3.1.0]hexane in pharmaceutically acceptable salt form is crystalline.

1.7 Any of Methods 1-1.6 wherein (1R,5S)-(+)-1-(3,4-dichlorophenyl)-3-azabicyclo[3.1.0]hexane, in free and/or pharmaceutically acceptable salt form, is Polymorph A substantially free of other polymorphic forms.

1.8 Any of Methods 1-1.6 wherein (1R,5S)-(+)-1-(3,4-dichlorophenyl)-3-azabicyclo[3.1.0]hexane, in free and/or pharmaceutically acceptable salt form, is Polymorph B substantially free of other polymorphic forms.

1.9 Any of Methods 1-1.6 wherein (1R,5S)-(+)-1-(3,4-dichlorophenyl)-3-azabicyclo[3.1.0]hexane, in free and/or pharmaceutically acceptable salt form, is Polymorph C substantially free of other polymorphic forms.

1.10 Any of Method 1 et seq. further comprising a treatment selected from one or more of surgery, transcutaneous electrical nerve stimulation, or neuroablation.

1.11 Any of Method 1 et seq. comprising administering 10 mg to 1800 mg, e.g., 25 mg to 1800 mg, e.g., 10 mg to 1600 mg, e.g., 10 mg to 1200 mg, e.g., 50 mg to 1200 mg, e.g., 75 mg to 1000 mg, e.g., 50 mg to 600 mg, e.g., 100 mg to 600 mg, e.g., 200 to 500 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

1.12 Any of Method 1 et seq. comprising administering 75 mg to 1000 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

1.13 Any of Method 1 et seq. comprising administering 50 mg to 600 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

1.14 Any of Method 1 et seq. comprising administering 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

1.15 Any of Method 1 et seq. comprising administering 50 mg to 200 mg of (1R,5S)-(+)-1-(3,4-dichlorophenyl)-3-azabicyclo[3.1.0]hexane, in free and/or pharmaceutically acceptable salt form.

1.16 Any of Method 1 et seq. comprising administering 100 mg to 200 mg of (1R,5S)-(+)-1-(3,4-dichlorophenyl)-3-azabicyclo[3.1.0]hexane, in free and/or pharmaceutically acceptable salt form.

1.17 Any of Method 1 et seq. comprising administering (1R,5S)-(+)-1-(3,4-dichlorophenyl)-3-azabicyclo[3.1.0]hexane, in free and/or pharmaceutically acceptable salt form, once, twice, three, or four times daily.

1.18 Any of Method 1 et seq. comprising administering (1R,5S)-(+)-1-(3,4-dichlorophenyl)-3-azabicyclo[3.1.0]hexane, in free and/or pharmaceutically acceptable salt form, once daily.

1.19 Any of Method 1 et seq. comprising administering (1R,5S)-(+)-1-(3,4-dichlorophenyl)-3-azabicyclo[3.1.0]hexane, in free and/or pharmaceutically acceptable salt form, twice daily.

1.20 Any of Method 1 et seq. comprising administering (1R,5S)-(+)-1-(3,4-dichlorophenyl)-3-azabicyclo[3.1.0]hexane, in free and/or pharmaceutically acceptable salt form, three times daily.

1.21 Any of Method 1 et seq. comprising administering (1R,5S)-(+)-1-(3,4-dichlorophenyl)-3-azabicyclo[3.1.0]hexane, in free and/or pharmaceutically acceptable salt form, four times daily.

1.22 Any of Method 1 et seq. wherein the pain is chronic pain.

1.23 Any of Method 1 et seq. wherein the pain is neuropathic pain.

1.24 Any of Method 1 et seq. further comprising administering a second therapeutic agent.

1.25 Method 1.24 wherein the second therapeutic agent is acetaminophen, e.g., as described in any of Methods 4 et seq. vide infra.

1.26 Method 1.24 wherein the second therapeutic agent is a non-steroidal anti-inflammatory drug, e.g., as described in any of Methods 5 et seq. vide infra.

1.27 Method 1.24 wherein the second therapeutic agent is a tricyclic antidepressant, e.g., amitriptyline.

Also provided herein is a method (Method 2) of treating pain comprising administering to a patient (e.g., human) in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the patient has compromised liver function.

2.1 Method 2 wherein the effective amount of (1R,5S)-(+)-1-(3,4-dichlorophenyl)-3-azabicyclo[3.1.0]hexane, in free and/or pharmaceutically acceptable salt form, comprises less than or equal to 2% w/w of the corresponding (−) enantiomer.

2.2 Method 2 or 2.1 wherein the effective amount of (1R,5S)-(+)-1-(3,4-dichlorophenyl)-3-azabicyclo[3.1.0]hexane, in free and/or pharmaceutically acceptable salt form, comprises less than or equal to 1% w/w of the corresponding (−) enantiomer.

2.3 Any of Method 2 et seq. wherein (1R,5S)-(+)-1-(3,4-dichlorophenyl)-3-azabicyclo[3.1.0]hexane is in pharmaceutically acceptable salt form.

2.4 Any of Method 2 et seq. wherein (1R,5S)-(+)-1-(3,4-dichlorophenyl)-3-azabicyclo[3.1.0]hexane in pharmaceutically acceptable salt form is an acid addition salt.

2.5 Any of Method 2 et seq. wherein (1R,5S)-(+)-1-(3,4-dichlorophenyl)-3-azabicyclo[3.1.0]hexane in pharmaceutically acceptable salt form is (1R,5S)-(+)-1-(3,4-dichlorophenyl)-3-azabicyclo[3.1.0]hexane hydrochloride.

2.6 Any of Method 2 et seq. wherein (1R,5S)-(+)-1-(3,4-dichlorophenyl)-3-azabicyclo[3.1.0]hexane in pharmaceutically acceptable salt form is crystalline.

2.7 Any of Methods 2-2.6 wherein (1R,5S)-(+)-1-(3,4-dichlorophenyl)-3-azabicyclo[3.1.0]hexane, in free and/or pharmaceutically acceptable salt form, is Polymorph A substantially free of other polymorphic forms.

2.8 Any of Methods 2-2.6 wherein (1R,5S)-(+)-1-(3,4-dichlorophenyl)-3-azabicyclo[3.1.0]hexane, in free and/or pharmaceutically acceptable salt form, is Polymorph B substantially free of other polymorphic forms.

2.9 Any of Methods 2-2.6 wherein (1R,5S)-(+)-1-(3,4-dichlorophenyl)-3-azabicyclo[3.1.0]hexane, in free and/or pharmaceutically acceptable salt form, is Polymorph C substantially free of other polymorphic forms.

2.10 Any of Method 2 et seq. comprising administering 10 mg to 1800 mg, e.g., 25 mg to 1800 mg, e.g., 10 mg to 1600 mg, e.g., 10 mg to 1200 mg, e.g., 50 mg to 1200 mg, e.g., 75 mg to 1000 mg, e.g., 50 mg to 600 mg, e.g., 100 mg to 600 mg, e.g., 200 mg to 500 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

2.11 Any of Method 2 et seq. comprising administering 75 mg to 1000 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

2.12 Any of Method 2 et seq. comprising administering 50 mg to 600 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

2.13 Any of Method 2 et seq. comprising administering 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

2.14 Any of Method 2 et seq. comprising administering 50 mg to 200 mg of (1R,5S)-(+)-1-(3,4-dichlorophenyl)-3-azabicyclo[3.1.0]hexane, in free and/or pharmaceutically acceptable salt form.

2.15 Any of Method 2 et seq. comprising administering 100 mg to 200 mg of (1R,5S)-(+)-1-(3,4-dichlorophenyl)-3-azabicyclo[3.1.0]hexane, in free and/or pharmaceutically acceptable salt form.

2.16 Any of Method 2 et seq. comprising administering (1R,5S)-(+)-1-(3,4-dichlorophenyl)-3-azabicyclo[3.1.0]hexane, in free and/or pharmaceutically acceptable salt form, once, twice, three, or four times daily.

2.17 Any of Method 2 et seq. comprising administering (1R,5S)-(+)-1-(3,4-dichlorophenyl)-3-azabicyclo[3.1.0]hexane, in free and/or pharmaceutically acceptable salt form, once daily.

2.18 Any of Method 2 et seq. comprising administering (1R,5S)-(+)-1-(3,4-dichlorophenyl)-3-azabicyclo[3.1.0]hexane, in free and/or pharmaceutically acceptable salt form, twice daily.

2.19 Any of Method 2 et seq. comprising administering (1R,5S)-(+)-1-(3,4-dichlorophenyl)-3-azabicyclo[3.1.0]hexane, in free and/or pharmaceutically acceptable salt form, three times daily.

2.20 Any of Method 2 et seq. comprising administering (1R,5S)-(+)-1-(3,4-dichlorophenyl)-3-azabicyclo[3.1.0]hexane, in free and/or pharmaceutically acceptable salt form, four times daily.

2.21 Any of Method 2 et seq. wherein the compromised liver function is a result of previous administration of one or more hepatotoxic medications.

2.22 Any of Method 2 et seq. wherein the compromised liver function is a result of concurrent or sequential administration of one or more hepatotoxic medications.

2.23 Any of Method 2 et seq. wherein the compromised liver function is a result of concurrent administration of one or more hepatotoxic medications.

2.24 Any of Method 2 et seq. wherein the compromised liver function is a result of sequential administration of one or more hepatotoxic medications.

2.25 Any of Method 2 et seq. further comprising a treatment selected from one or more of surgery, transcutaneous electrical nerve stimulation, or neuroablation.

2.26 Any of Method 2 et seq. wherein the pain is chronic pain.

2.27 Any of Method 2 et seq. wherein the pain is neuropathic pain.

2.28 Any of Method 2 et seq. further comprising administering a second therapeutic agent.

2.29 Method 2.28 wherein the second therapeutic agent is acetaminophen, e.g., as described in any of Methods 4 et seq. vide infra.

2.30 Method 2.28 wherein the second therapeutic agent is a non-steroidal anti-inflammatory drug, e.g., as described in any of Methods 5 et seq. vide infra.

2.31 Method 2.28 wherein the second therapeutic agent is a tricyclic antidepressant, e.g., amitriptyline.

Also provided herein is a method (Method 3) of treating pain comprising administering to a patient (e.g., human) in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the patient is a codeine non-responder.

3.1 Method 3 wherein the effective amount of (1R,5S)-(+)-1-(3,4-dichlorophenyl)-3-azabicyclo[3.1.0]hexane, in free and/or pharmaceutically acceptable salt form, comprises less than or equal to 2% w/w of the corresponding (−) enantiomer.

3.2 Method 3 or 3.1 wherein the effective amount of (1R,5S)-(+)-1-(3,4-dichlorophenyl)-3-azabicyclo[3.1.0]hexane, in free and/or pharmaceutically acceptable salt form, comprises less than or equal to 1% w/w of the corresponding (−) enantiomer.

3.3 Any of Method 3 et seq. wherein the (1R,5S)-(+)-1-(3,4-dichlorophenyl)-3-azabicyclo[3.1.0]hexane is in pharmaceutically acceptable salt form.

3.4 Any of Method 3 et seq. wherein the (1R,5S)-(+)-1-(3,4-dichlorophenyl)-3-azabicyclo[3.1.0]hexane in pharmaceutically acceptable salt form is an acid addition salt.

3.5 Any of Method 3 et seq. wherein the (1R,5S)-(+)-1-(3,4-dichlorophenyl)-3-azabicyclo[3.1.0]hexane in pharmaceutically acceptable salt form is (1R,5S)-(+)-1-(3,4-dichlorophenyl)-3-azabicyclo[3.1.0]hexane hydrochloride.

3.6 Any of Method 3 et seq. wherein the (1R,5S)-(+)-1-(3,4-dichlorophenyl)-3-azabicyclo[3.1.0]hexane in pharmaceutically acceptable salt form is crystalline.

3.7 Any of Methods 3-3.6 wherein the (1R,5S)-(+)-1-(3,4-dichlorophenyl)-3-azabicyclo[3.1.0]hexane, in free and/or pharmaceutically acceptable salt form, is Polymorph A substantially free of other polymorphic forms.

3.8 Any of Methods 3-3.6 wherein the (1R,5S)-(+)-1-(3,4-dichlorophenyl)-3-azabicyclo[3.1.0]hexane, in free and/or pharmaceutically acceptable salt form, is Polymorph B substantially free of other polymorphic forms.

3.9 Any of Methods 3-3.6 wherein the (1R,5S)-(+)-1-(3,4-dichlorophenyl)-3-azabicyclo[3.1.0]hexane, in free and/or pharmaceutically acceptable salt form, is Polymorph C substantially free of other polymorphic forms.

3.10 Any of Method 3 et seq. comprising administering 10 mg to 1800 mg, e.g., 25 mg to 1800 mg, e.g., 10 mg to 1600 mg, e.g., 10 mg to 1200 mg, e.g., 50 mg to 1200 mg, e.g., 75 mg to 1000 mg, e.g., 50 mg to 600 mg, e.g., 100 mg to 600 mg, e.g., 200 mg to 500 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

3.11 Any of Method 3 et seq. comprising administering 75 mg to 1000 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

3.12 Any of Method 3 et seq. comprising administering 50 mg to 600 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

3.13 Any of Method 3 et seq. comprising administering 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

3.14 Any of Method 3 et seq. comprising administering 50 mg to 200 mg of (1R,5S)-(+)-1-(3,4-dichlorophenyl)-3-azabicyclo[3.1.0]hexane, in free and/or pharmaceutically acceptable salt form.

3.15 Any of Method 3 et seq. comprising administering 100 mg to 200 mg of (1R,5S)-(+)-1-(3,4-dichlorophenyl)-3-azabicyclo[3.1.0]hexane, in free and/or pharmaceutically acceptable salt form.

3.16 Any of Method 3 et seq. comprising administering (1R,5S)-(+)-1-(3,4-dichlorophenyl)-3-azabicyclo[3.1.0]hexane, in free and/or pharmaceutically acceptable salt form, once, twice, three, or four times daily.

3.17 Any of Method 3 et seq. comprising administering (1R,5S)-(+)-1-(3,4-dichlorophenyl)-3-azabicyclo[3.1.0]hexane, in free and/or pharmaceutically acceptable salt form, once daily.

3.18 Any of Method 3 et seq. comprising administering (1R,5S)-(+)-1-(3,4-dichlorophenyl)-3-azabicyclo[3.1.0]hexane, in free and/or pharmaceutically acceptable salt form, twice daily.

3.19 Any of Method 3 et seq. comprising administering (1R,5S)-(+)-1-(3,4-dichlorophenyl)-3-azabicyclo[3.1.0]hexane, in free and/or pharmaceutically acceptable salt form, three times daily.

3.20 Any of Method 3 et seq. comprising administering (1R,5S)-(+)-1-(3,4-dichlorophenyl)-3-azabicyclo[3.1.0]hexane, in free and/or pharmaceutically acceptable salt form, four times daily.

3.21 Any of Method 3 et seq. further comprising a treatment selected from one or more of surgery, transcutaneous electrical nerve stimulation, or neuroablation.

3.22 Any of Method 3 et seq. wherein the pain is chronic pain.

3.23 Any of Method 3 et seq. wherein the pain is neuropathic pain.

3.24 Any of Method 3 et seq. further comprising administering a second therapeutic agent.

3.25 Method 3.24 wherein the second therapeutic agent is acetaminophen, e.g., as described in any of Methods 4 et seq. vide infra.

3.26 Method 3.24 wherein the second therapeutic agent is a non-steroidal anti-inflammatory drug, e.g., as described in any of Methods 5 et seq. vide infra.

3.27 Method 3.24 wherein the second therapeutic agent is a tricyclic antidepressant, e.g., amitriptyline.

Also provided herein is a method (Method 4) of treating pain comprising concurrently or sequentially (in any order) administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) acetaminophen.

4.1 Method 4 wherein (1R,5S)-(+)-1-(3,4-dichlorophenyl)-3-azabicyclo[3.1.0]hexane, in free and/or pharmaceutically acceptable salt form, comprises less than or equal to 2% w/w of the corresponding (−) enantiomer.

4.2 Method 4 or 4.1 wherein (1R,5S)-(+)-1-(3,4-dichlorophenyl)-3-azabicyclo[3.1.0]hexane, in free and/or pharmaceutically acceptable salt form, comprises less than or equal to 1% w/w of the corresponding (−) enantiomer.

4.3 Any of Method 4 et seq. wherein (1R,5S)-(+)-1-(3,4-dichlorophenyl)-3-azabicyclo[3.1.0]hexane is in pharmaceutically acceptable salt form.

4.4 Any of Method 4 et seq. wherein (1R,5S)-(+)-1-(3,4-dichlorophenyl)-3-azabicyclo[3.1.0]hexane in pharmaceutically acceptable salt form is an acid addition salt.

4.5 Any of Method 4 et seq. wherein (1R,5S)-(+)-1-(3,4-dichlorophenyl)-3-azabicyclo[3.1.0]hexane in pharmaceutically acceptable salt form is (1R,5S)-(+)-1-(3,4-dichlorophenyl)-3-azabicyclo[3.1.0]hexane hydrochloride.

4.6 Any of Method 4 et seq. wherein (1R,5S)-(+)-1-(3,4-dichlorophenyl)-3-azabicyclo[3.1.0]hexane in pharmaceutically acceptable salt form is crystalline.

4.7 Any of Methods 4-4.6 wherein (1R,5S)-(+)-1-(3,4-dichlorophenyl)-3-azabicyclo[3.1.0]hexane, in free and/or pharmaceutically acceptable salt form, is Polymorph A substantially free of other polymorphic forms.

4.8 Any of Methods 4-4.6 wherein (1R,5S)-(+)-1-(3,4-dichlorophenyl)-3-azabicyclo[3.1.0]hexane, in free and/or pharmaceutically acceptable salt form, is Polymorph B substantially free of other polymorphic forms.

4.9 Any of Methods 4-4.6 wherein (1R,5S)-(+)-1-(3,4-dichlorophenyl)-3-azabicyclo[3.1.0]hexane, in free and/or pharmaceutically acceptable salt form, is Polymorph C substantially free of other polymorphic forms.

4.10 Any of Method 4 et seq. comprising administering 10 mg to 1800 mg, e.g., 25 mg to 1800 mg, e.g., 10 mg to 1600 mg, e.g., 10 mg to 1200 mg, e.g., 50 mg to 1200 mg, e.g., 75 mg to 1000 mg, e.g., 50 mg to 600 mg, e.g., 100 mg to 600 mg, e.g., 200 mg to 500 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

4.11 Any of Method 4 et seq. comprising administering 75 mg to 1000 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

4.12 Any of Method 4 et seq. comprising administering 50 mg to 600 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

4.13 Any of Method 4 et seq. comprising administering 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

4.14 Any of Method 4 et seq. comprising administering 50 mg to 200 mg of (1R,5S)-(+)-1-(3,4-dichlorophenyl)-3-azabicyclo[3.1.0]hexane, in free and/or pharmaceutically acceptable salt form.

4.15 Any of Method 4 et seq. comprising administering 100 mg to 200 mg of (1R,5S)-(+)-1-(3,4-dichlorophenyl)-3-azabicyclo[3.1.0]hexane, in free and/or pharmaceutically acceptable salt form.

4.16 Any of Method 4 et seq. comprising administering (1R,5S)-(+)-1-(3,4-dichlorophenyl)-3-azabicyclo[3.1.0]hexane, in free and/or pharmaceutically acceptable salt form, once, twice, three, or four times daily.

4.17 Any of Method 4 et seq. comprising administering (1R,5S)-(+)-1-(3,4-dichlorophenyl)-3-azabicyclo[3.1.0]hexane, in free and/or pharmaceutically acceptable salt form, once daily.

4.18 Any of Method 4 et seq. comprising administering (1R,5S)-(+)-1-(3,4-dichlorophenyl)-3-azabicyclo[3.1.0]hexane, in free and/or pharmaceutically acceptable salt form, twice daily.

4.19 Any of Method 4 et seq. comprising administering (1R,5S)-(+)-1-(3,4-dichlorophenyl)-3-azabicyclo[3.1.0]hexane, in free and/or pharmaceutically acceptable salt form, three times daily.

4.20 Any of Method 4 et seq. comprising administering (1R,5S)-(+)-1-(3,4-dichlorophenyl)-3-azabicyclo[3.1.0]hexane, in free and/or pharmaceutically acceptable salt form, four times daily.

4.21 Any of Method 4 et seq. comprising administering 10 mg to 4000 mg, e.g., 50 mg to 3000 mg, e.g., 50 mg to 2000 mg, e.g., 50 mg to 1600 mg, e.g., 50 mg to 1200 mg, e.g., 75 mg to 1000 mg, e.g., 50 mg to 600 mg, e.g., 100 mg to 600 mg, e.g., 200 mg to 400 mg, e.g., 300 mg to 600 mg, e.g., 325 mg to 650 mg, e.g., 100 mg to 200 mg of acetaminophen.

4.22 Any of Method 4 et seq. comprising administering 50 mg to 2000 mg, e.g., 50 mg to 1600 mg, e.g., 50 mg to 1200 mg, e.g., 75 mg to 1000 mg, e.g., 50 mg to 600 mg, e.g., 100 mg to 600 mg, e.g., 200 mg to 400 mg, e.g., 300 mg to 600 mg, e.g., 325 mg to 650 mg, e.g., 100 mg to 200 mg of acetaminophen.

4.23 Any of Method 4 et seq. comprising administering 50 mg to 1200 mg, e.g., 75 mg to 1000 mg, e.g., 50 mg to 600 mg, e.g., 100 mg to 600 mg, e.g., 200 mg to 400 mg, e.g., 300 mg to 600 mg, e.g., 325 mg to 650 mg, e.g., 100 mg to 200 mg of acetaminophen.

4.24 Any of Method 4 et seq. comprising administering 300 mg to 600 mg of acetaminophen.

4.25 Any of Method 4 et seq. comprising administering 325 mg to 650 mg of acetaminophen.

4.26 Any of Method 4 et seq. comprising administering acetaminophen once, twice, three, or four times daily.

4.27 Any of Method 4 et seq. comprising administering acetaminophen once daily.

4.28 Any of Method 4 et seq. comprising administering acetaminophen twice daily.

4.29 Any of Method 4 et seq. comprising administering acetaminophen three times daily.

4.30 Any of Method 4 et seq. comprising administering acetaminophen four times daily.

4.31 Any of Method 4 et seq. comprising administering (a) (1R,5S)-(+)-1-(3,4-dichlorophenyl)-3-azabicyclo[3.1.0]hexane, in free and/or pharmaceutically acceptable salt form, and (b) acetaminophen concurrently.

4.32 Method 4.31 comprising administering (a) (1R,5S)-(+)-1-(3,4-dichlorophenyl)-3-azabicyclo[3.1.0]hexane, in free and/or pharmaceutically acceptable salt form, and (b) acetaminophen within the same composition.

4.33 Method 4.31 comprising administering (a) (1R,5S)-(+)-1-(3,4-dichlorophenyl)-3-azabicyclo[3.1.0]hexane, in free and/or pharmaceutically acceptable salt form, and (b) acetaminophen simultaneously.

4.34 Any of Methods 4-4.30 comprising administering (a) (1R,5S)-(+)-1-(3,4-dichlorophenyl)-3-azabicyclo[3.1.0]hexane, in free and/or pharmaceutically acceptable salt form, and (b) acetaminophen sequentially.

4.35 Method 4.32 wherein the composition comprises 10 mg to 1800 mg, e.g., 25 mg to 1800 mg, e.g., 10 mg to 1600 mg, e.g., 10 mg to 1200 mg, e.g., 50 mg to 1200 mg, e.g., 75 mg to 1000 mg, e.g., 50 mg to 600 mg, e.g., 100 mg to 600 mg, e.g., 200 mg to 500 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form, and 10 mg to 4000 mg, e.g., 50 mg to 3000 mg, e.g., 50 mg to 2000 mg, e.g., 50 mg to 1600 mg, e.g., 50 mg to 1200 mg, e.g., 75 mg to 1000 mg, e.g., 50 mg to 600 mg, e.g., 100 mg to 600 mg, e.g., 200 mg to 400 mg, e.g., 300 mg to 600 mg, e.g., 325 mg to 650 mg, e.g., 100 mg to 200 mg of acetaminophen.

4.36 Method 4.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form and 300 mg to 600 mg of acetaminophen.

4.37 Method 4.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form and 325 mg to 650 mg of acetaminophen.

4.38 Any of Method 4 et seq. further comprising a treatment selected from one or more of surgery, transcutaneous electrical nerve stimulation, or neuroablation.

4.39 Any of Method 4 et seq. wherein the pain is chronic pain.

4.40 Any of Method 4 et seq. wherein the pain is neuropathic pain.

4.41 Any of Method 4 et seq. wherein the patient is a heavy drinker and/or binge drinker.

4.42 Any of Method 4 et seq. wherein the patient has compromised liver function.

4.43 Any of Method 4 et seq. wherein the patient is a codeine non-responder.

Also provided herein is a method (Method 5) of treating pain comprising concurrently or sequentially (in any order) administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) a non-steroidal anti-inflammatory drug.

5.1 Method 5 wherein (1R,5S)-(+)-1-(3,4-dichlorophenyl)-3-azabicyclo[3.1.0]hexane, in free and/or pharmaceutically acceptable salt form, comprises less than or equal to 2% w/w of the corresponding (−) enantiomer.

5.2 Method 5 or 5.1 wherein (1R,5S)-(+)-1-(3,4-dichlorophenyl)-3-azabicyclo[3.1.0]hexane, in free and/or pharmaceutically acceptable salt form, comprises less than or equal to 1% w/w of the corresponding (−) enantiomer.

5.3 Any of Method 5 et seq. wherein (1R,5S)-(+)-1-(3,4-dichlorophenyl)-3-azabicyclo[3.1.0]hexane is in pharmaceutically acceptable salt form.

5.4 Any of Method 5 et seq. wherein (1R,5S)-(+)-1-(3,4-dichlorophenyl)-3-azabicyclo[3.1.0]hexane in pharmaceutically acceptable salt form is an acid addition salt.

5.5 Any of Method 5 et seq. wherein (1R,5S)-(+)-1-(3,4-dichlorophenyl)-3-azabicyclo[3.1.0]hexane in pharmaceutically acceptable salt form is (1R,5S)-(+)-1-(3,4-dichlorophenyl)-3-azabicyclo[3.1.0]hexane hydrochloride.

5.6 Any of Method 5 et seq. wherein (1R,5S)-(+)-1-(3,4-dichlorophenyl)-3-azabicyclo[3.1.0]hexane in pharmaceutically acceptable salt form is crystalline.

5.7 Any of Methods 5-5.6 wherein (1R,5S)-(+)-1-(3,4-dichlorophenyl)-3-azabicyclo[3.1.0]hexane, in free and/or pharmaceutically acceptable salt form, is Polymorph A substantially free of other polymorphic forms.

5.8 Any of Methods 5-5.6 wherein (1R,5S)-(+)-1-(3,4-dichlorophenyl)-3-azabicyclo[3.1.0]hexane, in free and/or pharmaceutically acceptable salt form, is Polymorph B substantially free of other polymorphic forms.

5.9 Any of Methods 5-5.6 wherein (1R,5S)-(+)-1-(3,4-dichlorophenyl)-3-azabicyclo[3.1.0]hexane, in free and/or pharmaceutically acceptable salt form, is Polymorph C substantially free of other polymorphic forms.

5.10 Any of Method 5 et seq. comprising administering 10 mg to 1800 mg, e.g., 25 mg to 1800 mg, e.g., 10 mg to 1600 mg, e.g., 10 mg to 1200 mg, e.g., 50 mg to 1200 mg, e.g., 75 mg to 1000 mg, e.g., 50 mg to 600 mg, e.g., 100 mg to 600 mg, e.g., 200 mg to 500 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

5.11 Any of Method 5 et seq. comprising administering 75 mg to 1000 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

5.12 Any of Method 5 et seq. comprising administering 50 mg to 600 mg, e.g., 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

5.13 Any of Method 5 et seq. comprising administering 100 mg to 600 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form.

5.14 Any of Method 5 et seq. comprising administering 50 mg to 200 mg of (1R,5S)-(+)-1-(3,4-dichlorophenyl)-3-azabicyclo[3.1.0]hexane, in free and/or pharmaceutically acceptable salt form.

5.15 Any of Method 5 et seq. comprising administering 100 mg to 200 mg of (1R,5S)-(+)-1-(3,4-dichlorophenyl)-3-azabicyclo[3.1.0]hexane, in free and/or pharmaceutically acceptable salt form.

5.16 Any of Method 5 et seq. comprising administering (1R,5S)-(+)-1-(3,4-dichlorophenyl)-3-azabicyclo[3.1.0]hexane, in free and/or pharmaceutically acceptable salt form, once, twice, three, or four times daily.

5.17 Any of Method 5 et seq. comprising administering (1R,5S)-(+)-1-(3,4-dichlorophenyl)-3-azabicyclo[3.1.0]hexane, in free and/or pharmaceutically acceptable salt form, once daily.

5.18 Any of Method 5 et seq. comprising administering (1R,5S)-(+)-1-(3,4-dichlorophenyl)-3-azabicyclo[3.1.0]hexane, in free and/or pharmaceutically acceptable salt form, twice daily.

5.19 Any of Method 5 et seq. comprising administering (1R,5S)-(+)-1-(3,4-dichlorophenyl)-3-azabicyclo[3.1.0]hexane, in free and/or pharmaceutically acceptable salt form, three times daily.

5.20 Any of Method 5 et seq. comprising administering (1R,5S)-(+)-1-(3,4-dichlorophenyl)-3-azabicyclo[3.1.0]hexane, in free and/or pharmaceutically acceptable salt form, four times daily.

5.21 Any of Method 5 et seq. comprising administering 10 mg to 4000 mg, e.g., 50 mg to 3000 mg, e.g., 50 mg to 2000 mg, e.g., 50 mg to 1600 mg, e.g., 50 mg to 1200 mg, e.g., 75 mg to 1000 mg, e.g., 50 mg to 600 mg, e.g., 100 mg to 1000 mg, e.g., 200 mg to 800 mg, e.g., 100 mg to 660 mg, e.g., 100 mg to 600 mg, e.g., e.g., 200 mg to 800 mg, e.g., 250 mg to 550 mg, e.g., 200 mg to 400 mg, e.g., 300 mg to 600 mg, e.g., 325 mg to 650 mg, e.g., 325 mg to 500 mg, e.g., 100 mg to 200 mg of the non-steroidal anti-inflammatory drug.

5.22 Any of Method 5 et seq. comprising administering 50 mg to 2000 mg, e.g., 50 mg to 1600 mg, e.g., 50 mg to 1200 mg, e.g., 75 mg to 1000 mg, e.g., 50 mg to 600 mg, e.g., 100 mg to 600 mg, e.g., 200 mg to 400 mg, e.g., 300 mg to 600 mg, e.g., 325 mg to 650 mg, e.g., 100 mg to 200 mg of the non-steroidal anti-inflammatory drug.

5.23 Any of Method 5 et seq. comprising administering 50 mg to 1200 mg, e.g., 75 mg to 1000 mg, e.g., 50 mg to 600 mg, e.g., 100 mg to 600 mg, e.g., 200 mg to 400 mg, e.g., 300 mg to 600 mg, e.g., 325 mg to 650 mg, e.g., 100 mg to 200 mg of the a non-steroidal anti-inflammatory drug.

5.24 Any of Method 5 et seq. comprising administering 300 mg to 600 mg of the non-steroidal anti-inflammatory drug.

5.25 Any of Method 5 et seq. comprising administering 325 mg to 650 mg of the non-steroidal anti-inflammatory drug.

5.26 Any of Method 5 et seq. comprising administering the non-steroidal anti-inflammatory drug once, twice, three, or four times daily.

5.27 Any of Method 5 et seq. comprising administering the non-steroidal anti-inflammatory drug once daily.

5.28 Any of Method 5 et seq. comprising administering the non-steroidal anti-inflammatory drug twice daily.

5.29 Any of Method 5 et seq. comprising administering the non-steroidal anti-inflammatory drug three times daily.

5.30 Any of Method 5 et seq. comprising administering the non-steroidal anti-inflammatory drug four times daily.

5.31 Any of Method 5 et seq. wherein (a) (1R,5S)-(+)-1-(3,4-dichlorophenyl)-3-azabicyclo[3.1.0]hexane, in free and/or pharmaceutically acceptable salt form, and (b) the non-steroidal anti-inflammatory drug are administered concurrently.

5.32 Method 5.31 wherein (a) (1R,5S)-(+)-1-(3,4-dichlorophenyl)-3-azabicyclo[3.1.0]hexane, in free and/or pharmaceutically acceptable salt form, and (b) the non-steroidal anti-inflammatory drug are within the same composition.

5.33 Method 5.31 wherein (a) (1R,5S)-(+)-1-(3,4-dichlorophenyl)-3-azabicyclo[3.1.0]hexane, in free and/or pharmaceutically acceptable salt form, and (b) the non-steroidal anti-inflammatory drug are administered simultaneously.

5.34 Any of Methods 5-5.30 wherein (a) (1R,5S)-(+)-1-(3,4-dichlorophenyl)-3-azabicyclo[3.1.0]hexane, in free and/or pharmaceutically acceptable salt form, and (b) the non-steroidal anti-inflammatory drug are administered sequentially.

5.35 Method 5.32 wherein the composition comprises 10 mg to 1800 mg, e.g., 25 mg to 1800 mg, e.g., 10 mg to 1600 mg, e.g., 10 mg to 1200 mg, e.g., 50 mg to 1200 mg, e.g., 75 mg to 1000 mg, e.g., 50 mg to 600 mg, e.g., 100 mg to 600 mg, e.g., 200 mg to 500 mg, e.g., 200 mg to 400 mg, e.g., 100 mg to 200 mg of (1R,5S)-(+)-1-(3,4-dichlorophenyl)-3-azabicyclo[3.1.0]hexane, in free and/or pharmaceutically acceptable salt form, and 10 mg to 4000 mg, e.g., 50 mg to 3000 mg, e.g., 50 mg to 2000 mg, e.g., 50 mg to 1600 mg, e.g., 50 mg to 1200 mg, e.g., 75 mg to 1000 mg, e.g., 50 mg to 600 mg, e.g., 100 mg to 1000 mg, e.g., 100 mg to 660 mg, e.g., 100 mg to 600 mg, e.g., 200 mg to 400 mg, e.g., 300 mg to 600 mg, e.g., 325 mg to 650 mg, e.g., 325 mg to 500 mg, e.g., 100 mg to 200 mg of the non-steroidal anti-inflammatory drug.

5.36 Method 5.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form and 300 mg to 600 mg of the non-steroidal anti-inflammatory drug.

5.37 Method 5.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form, and 325 mg to 500 mg of the non-steroidal anti-inflammatory drug.

5.38 Method 5.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form, and 100 mg to 1000 mg of the non-steroidal anti-inflammatory drug.

5.39 Method 5.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form, and 200 mg to 800 mg of the non-steroidal anti-inflammatory drug.

5.40 Method 5.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form, and 100 mg to 600 mg of the non-steroidal anti-inflammatory drug.

5.41 Method 5.35 wherein the composition comprises 50 mg to 200 mg of (1R,5S)-(+)-1-(3,4-dichlorophenyl)-3-azabicyclo[3.1.0]hexane, in free and/or pharmaceutically acceptable salt form, and 250 mg to 550 mg of the non-steroidal anti-inflammatory drug.

5.42 Any of Method 5 et seq. wherein the non-steroidal anti-inflammatory drug is aspirin, ibuprofen, or naproxen.

5.43 Method 5.36 or 5.37 wherein the non-steroidal anti-inflammatory drug is aspirin.

5.44 Method 5.38 or 5.39 wherein the non-steroidal anti-inflammatory drug is ibuprofen.

5.45 Method 5.40 or 5.41 wherein the non-steroidal anti-inflammatory drug is naproxen.

5.46 Any of Method 5 et seq. further comprising a treatment selected from one or more of surgery, transcutaneous electrical nerve stimulation, or neuroablation.
5.47 Any of Method 5 et seq. wherein the pain is chronic pain.
5.48 Any of Method 5 et seq. wherein the pain is neuropathic pain.
5.49 Any of Method 5 et seq. wherein the patient is a heavy drinker and/or binge drinker.
5.50 Any of Method 5 et seq. wherein the patient has compromised liver function.
5.51 Any of Method 5 et seq. wherein the patient is a codeine non-responder.

Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective and may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

In one embodiment, a patient who suffers from compromised liver function is contraindicated from taking one or more common analgesic medications (e.g., acetaminophen or NSAIDs) due to the risk of further liver damage, and such a patient may benefit from treatment with (1R,5S)-(+)-1-(3,4-dichlorophenyl)-3-azabicyclo[3.1.0]hexane, in free and/or pharmaceutically acceptable salt form, in combination with a reduced or subthreshold amount of the common analgesic medication.

Also provided herein is use of (1R,5S)-(+)-1-(3,4-dichlorophenyl)-3-azabicyclo[3.1.0]hexane, in free and/or pharmaceutically acceptable salt form, for treating pain, for example, for use in any of Method 1 et seq., Method 2 et seq., Method 3 et seq., Method 4 et seq., or Method 5 et seq.

Also provided herein is (1R,5S)-(+)-1-(3,4-dichlorophenyl)-3-azabicyclo[3.1.0]hexane, in free and/or pharmaceutically acceptable salt form, in the manufacture of a medicament for treating pain, for example, for use in any of Method 1 et seq., Method 2 et seq., Method 3 et seq., Method 4 et seq., or Method 5 et seq.

Also provided is a pharmaceutical composition comprising (1R,5S)-(+)-1-(3,4-dichlorophenyl)-3-azabicyclo[3.1.0]hexane, in free and/or pharmaceutically acceptable salt form, in combination with a pharmaceutically acceptable diluent or carrier for use in treating pain, for example, for use in any of Method 1 et seq., Method 2 et seq., Method 3 et seq., Method 4 et seq., or Method 5 et seq.

A dose or method of administration of the dose of the present disclosure is not particularly limited. Dosages employed in practicing the present disclosure will of course vary depending, e.g. on the particular disease or condition to be treated, the particular compound used, the mode of administration, and the therapy desired. (1R,5S)-(+)-1-(3,4-dichlorophenyl)-3-azabicyclo[3.1.0]hexane, in free and/or pharmaceutically acceptable salt form, may be administered by any suitable route, including oral, buccal, nasal, aerosol, topical, transdermal, mucosal, injectable, slow release, controlled release, although various other known delivery routes, devices and methods can likewise be employed.

Pharmaceutical compositions comprising (1R,5S)-(+)-1-(3,4-dichlorophenyl)-3-azabicyclo[3.1.0]hexane, in free and/or pharmaceutically acceptable salt form, may be prepared using conventional diluents or excipients and techniques known in the galenic art. Thus oral dosage forms may include tablets, capsules, solutions, suspensions and the like.

In accordance with these exemplary embodiments, (1R,5S)-(+)-1-(3,4-dichlorophenyl)-3-azabicyclo[3.1.0]hexane, in free and/or pharmaceutically acceptable salt form, is administered in an effective amount to alleviate pain. In general oral dosages of from about 0.5 mg/kg to about 20 mg/kg per day are used. However the amount of (1R,5S)-(+)-1-(3,4-dichlorophenyl)-3-azabicyclo[3.1.0]hexane, in free and/or pharmaceutically acceptable salt form, in the oral unit dose to be administered will depend to a large extent on the amount of pain and the weight of the patient and of course be subject to the physician's judgment. For example, for patients of from about 60 kg to about 80 kg unit oral dosage forms containing from about 100 mg to about 600 mg will often be utilized, with dosages of about 200 mg to 400 mg being generally preferred.

In other embodiments of this disclosure, an effective amount of (1R,5S)-(+)-1-(3,4-dichlorophenyl)-3-azabicyclo [3.1.0]hexane, in free and/or pharmaceutically acceptable salt form, may range from about 1 to 1200 mg, 50 to 1000 mg, 75 to 900 mg, 100 to 800 mg, or 150 to 600 mg. In certain embodiments, the effective amount will be selected within narrower ranges of, for example, 10 to 25 mg, 30 to 50 mg, 75 to 100 mg, 100 to 150 mg, 150 to 250 mg, 200 to 400 mg, 250 to 500 mg, or 400 to 600 mg. These and other effective amounts may be administered in a single dose, or in the form of multiple daily, weekly or monthly doses, for example in a dosing regimen comprising from 1 to 5, or 2 to 3, doses administered per day, per week, or per month. In exemplary embodiments, dosages of 10 to 25 mg, 30 to 50 mg, 75 to 100 mg, 100 to 200 mg, or 250 to 500 mg, are administered one, two, three, or four times per day. In more detailed embodiments, dosages of 50-75 mg, 100-150 mg, 150-200 mg, 250-400 mg, or 400-600 mg are administered once daily, twice daily, or three times daily. In alternate embodiments, dosages are calculated based on body weight, and may be administered, for example, in amounts from about 0.5 mg/kg to about 30 mg/kg per day, 1 mg/kg to about 15 mg/kg per day, 1 mg/kg to about 10 mg/kg per day, 2 mg/kg to about 20 mg/kg per day, 2 mg/kg to about 10 mg/kg per day or 3 mg/kg to about 15 mg/kg per day.

Additional therapeutic agents may be useful in Methods 1-5 above, wherein the additional therapeutic agents are not contraindicated or already discussed for that Method. Additional therapeutic agents in this context include antidepressants, antiarrhythmics, antiepileptics, anti-convulsants, membrane-stabilizing drugs, opioids, NSAIDs, COX-2 inhibitors, K+ channel openers, topical anesthetics, acetaminophen, topical analgesics, central analgesics, N-methyl-D-aspartate receptor (NMDA) antagonists, and anti-inflammatories (See, e.g., R J. Baldessarini in Goodman & Gilman's The Pharmacological Basis of Therapeutics, 11th Edition, Chapters 17 and 18, McGraw-Hill, 2005 for a review). For instance, additional therapeutic agents include, but are not limited to, NSAIDs (e.g., aspirin and ibuprofen); COX-2 inhibitors; synthetic and natural opiates (e.g., oxycodone, meperidine, morphine, and codeine); mexiletine; baclofen; tramadol; antiarrhythmics; anticonvulsants (e.g., lamotrigine, gabapentin, valproic acid, valproate sodium, divalproex sodium, topiramate, famotodine, phenobarbital, metharbital, diphenylhydantoin, phenyloin, mephenyloin, ethotoin, mephobarbital, primidone, carbamazepine, ethosuximide, methsuximide, phensuximide, phenacemide, and trimethadione); benzodiazepines (e.g. diazepam, clonazepam, and clobazam); antiepileptics (e.g. sulthiame, acetazolamide, paramethadione, progabide, phenyloin sodium (e.g., dilantin), and diphenylan); capsaicin cream; magnesium sulfate injection; membrane-stabilizing drugs (e.g., lidocaine); N-methyl-D-aspartate receptor (NMDA) antagonists such as ketamine; as well as all other known analgesic drugs and drugs useful for treating symptoms of neuropathies, such as pregabalin, harkoseride, amitriptyline, milnacipran, venlafaxine, duloxetine, desipramine, and other related tricyclic antidepressants.

It is to be understood that this disclosure is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present disclosure will be limited only by the appended claims and equivalents thereof.

The following examples illustrate certain aspects of this disclosure, but are not intended to limit in any manner the scope of this disclosure.

Example 1

Formalin Paw Test

Male CD-1 (Crl.) mice weighing 24±2 g from BioLasco Taiwan (under Charles River Laboratories Technology licensee) are used. All animals are maintained in a controlled temperature (22° C.-24° C.) and humidity (60%-70%) environment with 12 hours light/dark cycles for at least one week in MDS Pharma Services—Taiwan Laboratory prior to being used. Free access to standard lab chow (MF-18 (Oriental Yeast Co., Ltd. Japan)) and RO water is granted. All aspects of this work including housing, experimentation and disposal of animals are performed in general accordance with the Guide for the Care and Use of Laboratory Animals (National Academy Press, Washington, D.C., 1996).

The mice are divided into three groups and given vehicle (2% Tween 80), 40 mg/kg of (1R,5S)-(+)-1-(3,4-dichlorophenyl)-3-azabicyclo[3.1.0]hexane hydrochloride (EB-1010) or 30 mg/kg of morphine orally 1 hour before subplantar injection of formalin (0.02 ml, 5% solution). The amount of paw licking time is then observed and recorded at 5-minute intervals during the following 0 to 30 minutes after injection of formalin. (See Hunskaar, S., Fasmer O. B. and Hole, K. Formalin test in mice, a useful technique for evaluating mild analgesics. J. Neuroscience Meth. 14: 69-76, 1985.)

Reduction of the formalin-induced hind paw licking time recorded at 5-minute intervals during the following 0- to 30-minute period after formalin injection by 50 percent or more (≥50%) indicates significant analgesic activity. Also, statistical analysis is performed by using one-way ANOVA followed by Dunnett's test to compare the test compound-treated and vehicle control groups. Significance is considered at $P<0.05$ level.

As can be seen in FIG. 1, (1R,5S)-(+)-1-(3,4-dichlorophenyl)-3-azabicyclo[3.1.0]hexane hydrochloride is as effective as morphine in the second phase (15-30 minutes) of the mouse formalin paw lick test model of persistent pain. Thus, (1R,5S)-(+)-1-(3,4-dichlorophenyl)-3-azabicyclo[3.1.0]hexane hydrochloride and compositions comprising (1R,5S)-(+)-1-(3,4-dichlorophenyl)-3-azabicyclo[3.1.0]hexane hydrochloride may be used to treat pain, for example, chronic pain in place of, for example, Vicodin and acetaminophen/codeine.

Example 2

Plasma Protein Binding

Human plasma protein binding of amitifadine ((1R,5S)-(+)-1-(3,4-dichlorophenyl)-3-azabicyclo[3.1.0]hexane hydrochloride) is determined by ADMETRx (Kalamazoo, Mich.) using an ultrafiltration technique. The samples containing various concentration of the test compound in DMSO are diluted into human plasma (Innovative Research, Inc., Novi, Mich.) to yield 1 or 10 µM final solute concentration. Samples of test drug in triplicate are mixed and incubated in Millipore Multiscreen filter plates with Ultracel-10 regenerated cellulose membranes for 60 minutes at 37° C. Following incubation, samples undergo centrifugation for 60 minutes at 2000×g and the filtrate is collected. Percent protein bound is determined from the concentration of free compound present in the filtrate following comparison to a standard curve of test drug. Aliquots of the filtrate are analyzed on the Waters Alliance 2795 HPLC utilizing a 3.5 µm Agilent ZORBAX Eclipse XBD-C18 50×2.1 column coupled with a Waters Quattro micro mass spectrometer (m/z 228.05>187.10). The flow rate is 1 ml/min and the column temperature is maintained at 50° C. The solvent is a gradient of solvent A composed of 0.1% formic acid in water and solvent B composed of acetonitrile with 0.07% formic acid.

The plasma protein binding of amitifadine has an average binding of 99.4% (Table 1). There is no appreciable difference in the percentage of amitifadine bound at 1 and 10 µM concentrations, indicating no saturation of the binding at tested concentrations. The recovery of amitifadine (mass balance) is close to 100% indicating no non-specific binding to the ultracentrifugation apparatus (data not shown). The plasma protein binding of the comparator caffeine is 31.5%, consistent with previous reports in the literature.

TABLE 1

Human plasma protein binding by amitifadine and caffeine

| Compound | Concentration, µM | % Bound |
|---|---|---|
| Amitifadine | 1 | 99.37 + 0.25 |
| Amitifadine | 10 | 99.47 + 0.06 |
| Caffeine | 1 | 27.0 + 2.0 |
| Caffeine | 10 | 35.9 + 1.2 |

The values are the mean and SEM of triplicate determinations.

Example 3

Caco-2 Bi-Directional Permeability Assay

The Caco-2 permeability of amitifadine is conducted by ADMETRx (Kalamazoo, Mich.). Aliquots of DMSO stock solution of drug are dissolved in Hanks Balanced Salt Solution containing 25 mM HEPES, pH 7.4 buffer with 0.05% polysorbate 80 to give target stock drug concentrations of 250 µM and 2.5% DMSO. Caco-2 cells are obtained from American Type Culture Collection (ATCC, Manassas, Va.) and are grown to confluence for 14-21 days on 1 µm filters in 24 well plates. Aliquots of drug are diluted in buffer to give 10 µM final concentration and <1% DMSO. The solutions are then transferred to either the apical or basolateral chamber of the permeability diffusion apparatus for incubation in an atmosphere of 95% air and 5% $CO_2$, relative humidity of 95%, and temperature of 37° C. Receiver solutions consist of buffer only. Sequential samples of transported solute are taken at 20 minute intervals in duplicate over 2 hours and the concentration of the transported compound is determined by HPLC-UV/MS. Test sample concentration is determined by LC/MS. Permeability coefficients are calculated for each sampling interval, and averages from the intervals are determined. The apparent permeability coefficient $P_{app}$ is calculated from the equation $$P_{app} = \frac{dQ}{dT} \times \frac{1}{A \times C_0},$$

where dQ/dt is the rate of permeation of drug across the cells, $C_0$ is the original concentration in donor compartment at time zero, and A is the area of the cell monolayer. Mass balance in the system is ascertained by comparing the sum of transported solute and remaining donor solute to the starting solution concentration. The integrity of the monolayers is verified by monitoring Lucifer yellow permeation and the known P-glycoprotein substrate Ac-D-Phe-(N-Me-D-Phe)$_2$-NH$_2$ is used as a positive control.

The bidirectional permeability of amitifadine across the Caco-2 monolayer is determined from 40 to 120 minutes. The result shows amitifadine (10 μM) is highly permeable in both the absorptive apical to basolateral (AP→BL) and the secretory basolateral to apical (BL→AP) directions with average apparent permeability coefficients of 69.2×10$^{-6}$ cm/s and of 127×10$^{-6}$ cm/s, respectively (Table 2). However, mass balance (total recovery) is only 62% in the AP→BL direction. The p-glycoprotein substrate Ac-D-Phe-(N-Me-D-Phe)$_2$-NH$_2$ has BL→AP permeability 4 fold greater than in the AP→BL direction. The transfer of Lucifer yellow is ≤0.05%, which confirms the integrity of the Caco-2 monolayer.

TABLE 2

Bidirectional permeability of amitifadine (10 μM) and Ac-D-Phe-(N-Me-D-Phe)$_2$-NH$_2$ (10 μM) in the absorptive apical to basolateral (AP→BL) and secretory basolateral to apical (BL→AP) phases

| Compound | PE$_{AP \rightarrow BL}$ 1 × 10$^{-6}$ cm/s (Mass balance %) | PE$_{BL \rightarrow AP}$ 1 × 10$^{-6}$ cm/s (Mass balance %) |
|---|---|---|
| Amitifadine | 69.2 (62%) | 127 (88%) |
| Ac-D-Phe-(N-Me-D-Phe)$_2$-NH$_2$ | 18.8 (96%) | 82.8 (104%) |

Values are average transport expressed as apparent permeability coefficient (PE) (1 × 10$^{-6}$ cm/s) and mass balance in percent of total drug on both sides of membrane.

Example 4

In Vitro Metabolism in Human Hepatocytes

Metabolism of amitifadine in human hepatocytes and detection of metabolites formed is conducted by XenoBiotic Laboratories, Inc. (Plainsboro, N.J.). Cryopreserved human hepatocytes (male) that are prepared by XenoTech, LLC (Lenexa, Kans.), are thawed on the day of use and resuspended in Waymouth's incubation media. The enzymatic activity of hepatocytes is monitored using 7-ethoxycoumarin and 7-hydroxycoumarin as substrates. Amitifadine is dissolved in methanol and added to the hepatocyte suspension with a final concentration of 87 μM containing 0.25% methanol. The incubations are carried out for 4 hours with 1×10$^6$ viable cells/ml. All incubations are conducted in an incubator maintained at 37° C. and in an atmosphere consisting of about 95% air and 5% CO$_2$; relative humidity is maintained at about 95%. Cell viability is checked using trypan blue exclusion method at 0, 1, and 4 hours of incubation, and 82% of the cells remain viable after 4 hour incubation. At 0 and 4 hour, cell suspensions are extracted using two volumes of ice cold methanol. After centrifugation, the extracts are stored at −20° C. until further sample processing. The solvent in the samples are dried under a stream of nitrogen, and resuspended in methanol:water (1:1) before analysis. The extracts of the 4 hour incubation mixture of amitifadine are analyzed by LC/electrospray ionization-mass spectrometry (LC/ESI-MS) using LCQ™ Ion Trap Mass Spectrometer in the positive and negative ion modes to screen for possible metabolites. Because amitifadine contains two chlorines, the unique pattern of $^{35}$Cl and $^{37}$Cl ion clusters is used for the determination and confirmation of molecular and fragment ions of the metabolites. The disappearance of the parent drug is estimated by comparison of the mass ion intensity (peak height) of amitifadine in the 0 and 4 hour incubations.

The extracts of the 4 hour incubation mixture are analyzed by liquid chromatography/electrospray ionization-mass spectrometry (LC/ESI-MS) in the positive and negative ion modes to screen for possible metabolites. HPLC Methods 1 and 2 find potential metabolites, and the HPLC and mass spectrometry systems are described in Table 3. The gradient for the HPLC system for Method 1 is shown in Table 4. The gradient for the HPLC system for Method 2 is shown in Table 5. The same instrumentation and methods in HPLC Method 1 are used in HPLC Method 2 with the exception that the mobile phases and gradient are 0.4% HCOOH in H$_2$O for mobile A and CH$_3$OH for mobile phase B. The mass spectrometer is LCQ™ Ion Trap Mass Spectrometer and is in either the positive or negative electrospray mode with the ion spray set at 4.5 kV. The capillary temperature is 250° C., the nitrogen sheath gas flow rate is ~80 unit, the auxiliary nitrogen gas flow rate is 20 unit, and the collision gas is helium.

TABLE 3

Mass spectrometry systems, columns, and parameters used for in vitro metabolism study in hepatocytes

| Item | Type |
|---|---|
| HPLC system | Waters ® 2695 Separations Module |
| UV Detector | Waters ® 486 at 254 nm |
| Column | Ace 3, C18, 3 μm, 150 × 4.6 mm |
| Guard column | RP-18, 7 μm, 15 × 3.2 mm column |
| Temperature | 35° C. |
| Autosampler temperature | 4° C. |
| Mobile phase A | 0.01M NH$_4$OAc in H$_2$O (pH ca. 6.7) |
| Mobile phase B | CH$_3$CN |

TABLE 4

Gradient table for Method 1 in vitro metabolism study in hepatocytes

| Time (min) | Flow (ml/min) | % A | % B |
|---|---|---|---|
| Initial | 0.7 | 100 | 0 |
| 3 | 0.7 | 100 | 0 |
| 8 | 0.7 | 90 | 10 |
| 58 | 0.7 | 65 | 35 |

TABLE 4-continued

Gradient table for Method 1 in vitro metabolism study in hepatocytes

| Time (min) | Flow (ml/min) | % A | % B |
|---|---|---|---|
| 65 | 0.7 | 0 | 100 |
| 70 | 0.7 | 0 | 100 |
| 72 | 0.7 | 100 | 0 |

TABLE 5

Gradient table for Method 2 in vitro metabolism study in hepatocytes

| Time (min) | Flow (ml/min) | % A | % B |
|---|---|---|---|
| Initial | 0.7 | 100 | 0 |
| 3 | 0.7 | 100 | 0 |
| 8 | 0.7 | 80 | 20 |
| 58 | 0.7 | 30 | 70 |
| 65 | 0.7 | 0 | 100 |
| 70 | 0.7 | 0 | 100 |
| 72 | 0.7 | 100 | 0 |

Figure 2:
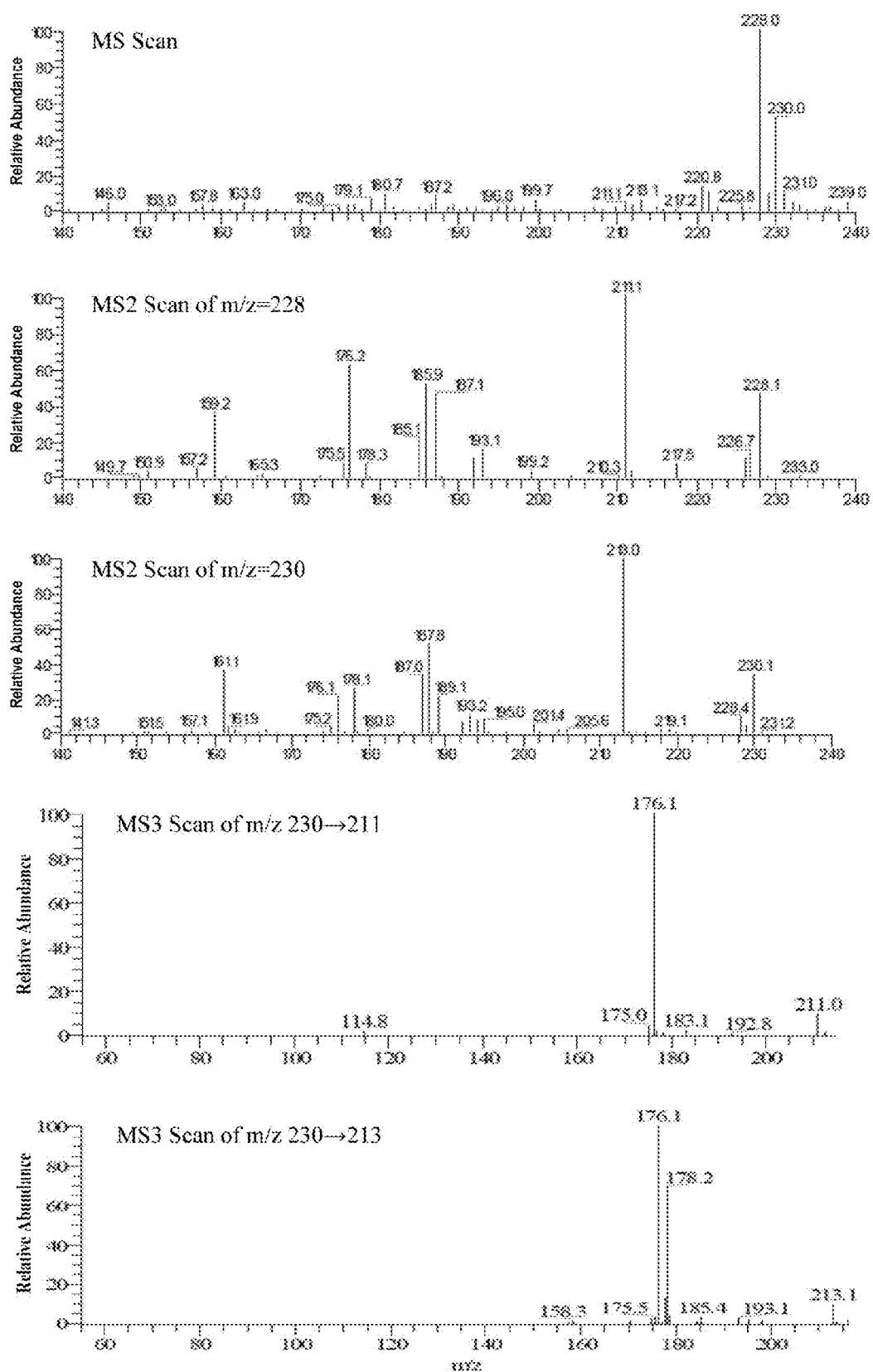
FIG. 2 is the MS spectra of amitifadine standard using methods described herein.
Figure 3:
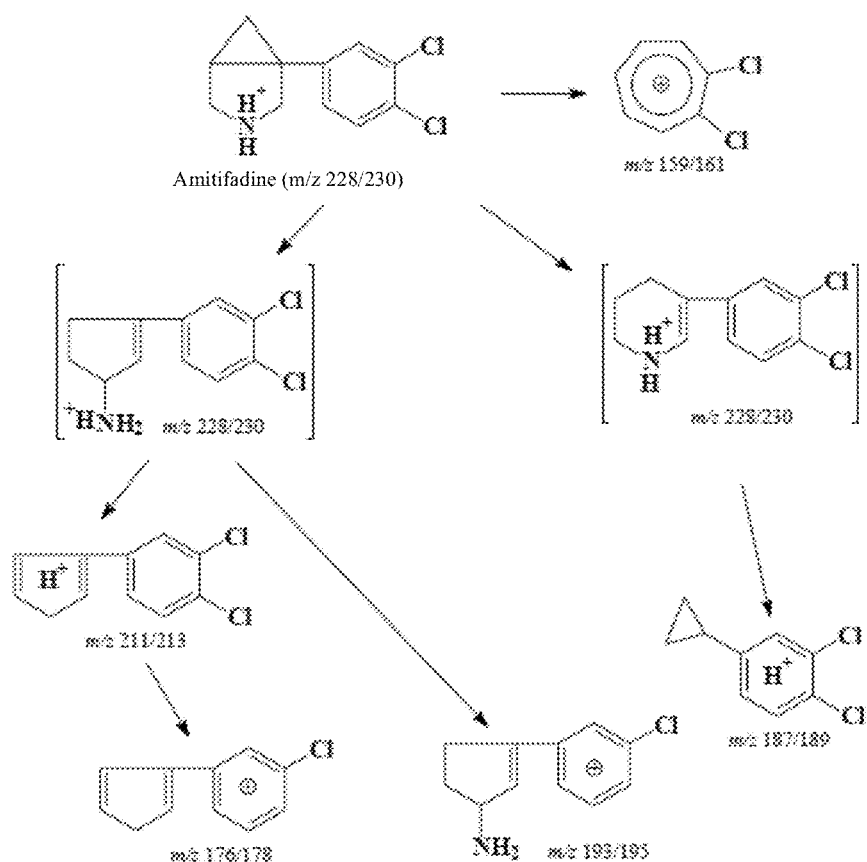
FIG. 3 is the proposed ion fragmentation of amitifadine.
Figure 4:
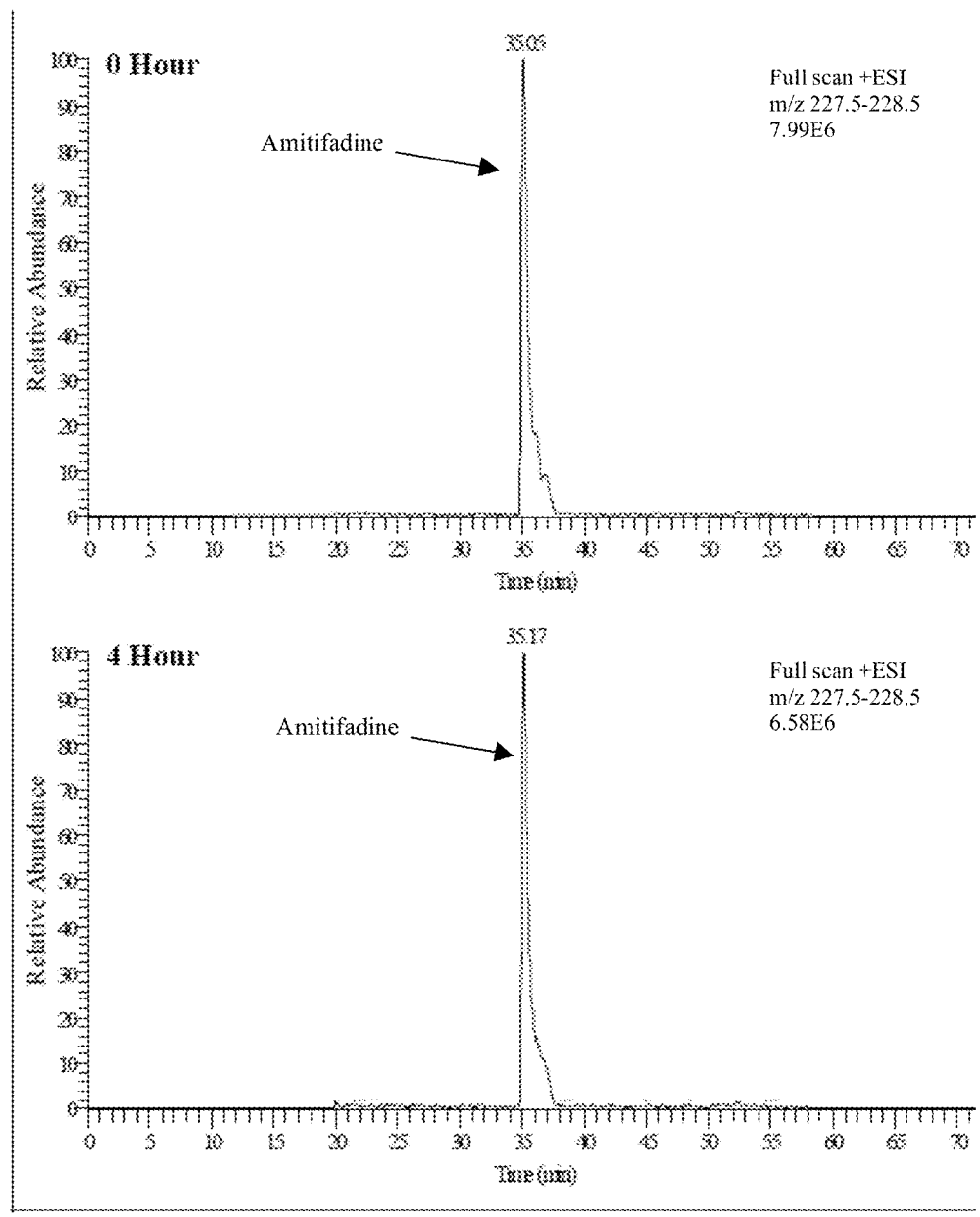
FIG. 4 is the extracted mass ion chromatograms of amitifadine in 0 and 4 hour human hepatocyte incubations using methods described herein. Data shown for each sample are extracted ion of full scans. +ESI: positive ion mode of electrospray ionization is used in this scan.
Figure 5:
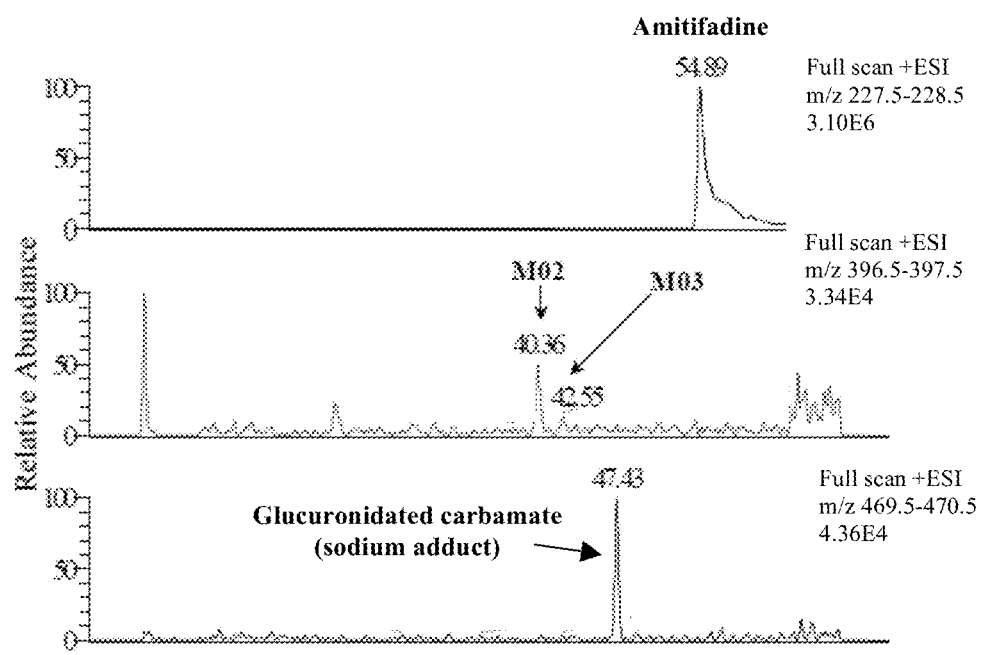
FIG. 5 is the extracted ion chromatograms of extract of 4 hour human hepatocyte incubation with amitifadine using methods described herein. Data shown for each sample are extracted ion of full scans. The +ESI: positive ion mode of electrospray ionization is used in this scan.
Figure 6:
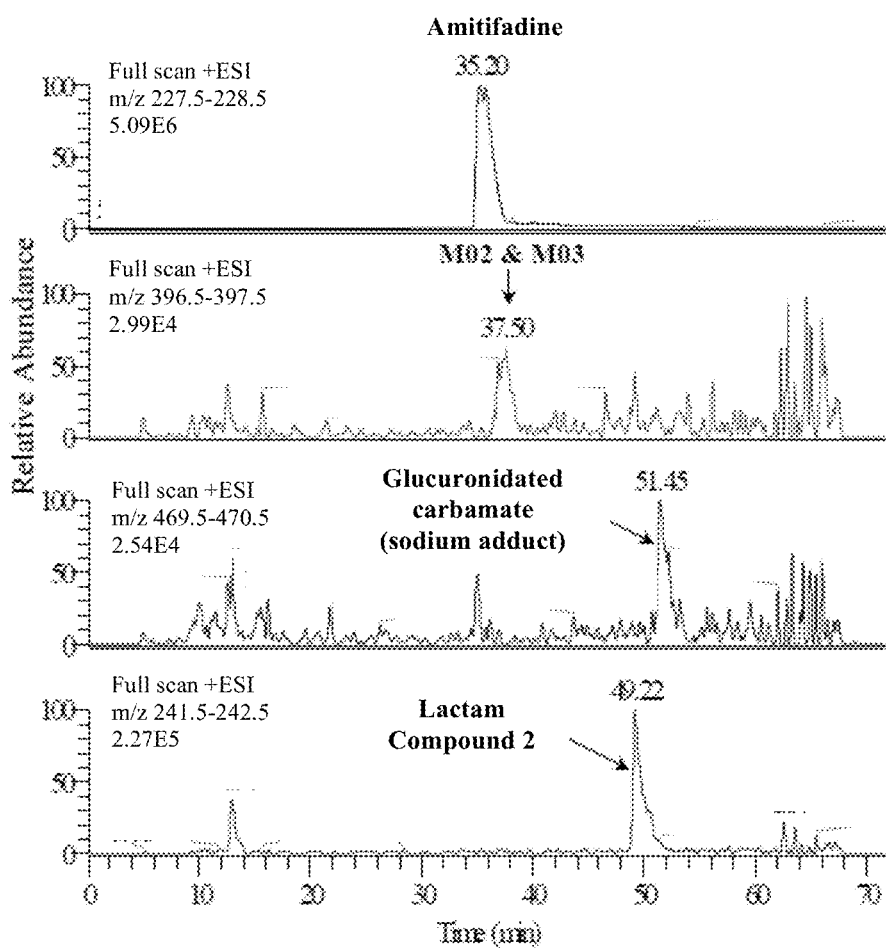
FIG. 6 is the extracted mass chromatograms of 4 hour human hepatocyte incubation with amitifadine using methods described herein. Data shown for each sample are extracted ion of full scans. The +ESI: positive ion mode of electrospray ionization is used in this scan.

The amitifadine standard is analyzed using LC/MS and the mass ion patterns generated are shown in FIG. 2. Based on the MS2 and MS3 ion fragment patterns, the proposed ion fragmentation pathways of amitifadine are in FIG. 3. At completion of a 4 hour incubation, 82% human hepatocytes remain viable as determined by the trypan blue exclusion method (data not shown). After 4 hours incubation with the human hepatocytes, 68.9% of 7-ethoxycoumarin (100 µM), and 99.1% of 7-hydroxycoumarin (100 µM) are metabolized, indicating the hepatocytes are metabolically active. The majority of amitifadine (82.4%) from the 87 µM initial concentration remains unchanged after 4 hour incubation based on the parent mass ion intensity (FIG. 4). Two different LC-MS/MS methods are conducted to screen for prominent amitifadine metabolites formed in human hepatocytes incubation samples and 4 different metabolites are detected (See FIGS. 5 and 6). The structures of the metabolites (Table 6) are proposed based on mass ion and fragment patterns (data not shown).

TABLE 6

Proposed structure, molecular weight, and retention times of putative metabolites formed from metabolism of amitifadine by human hepatocytes.

| Compound | Proposed structure | $^{35}$Cl—MW | Retention time, min (using methods described herein) |
|---|---|---|---|
| Amitifadine | 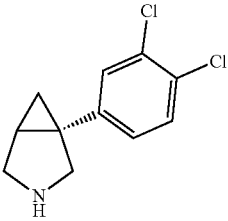 [SMILES: Clc1ccc([C@]23CNCC2C3)cc1Cl] | 227 | ~55.0<br>~35.8 |
| Glucuronidated carbamate | 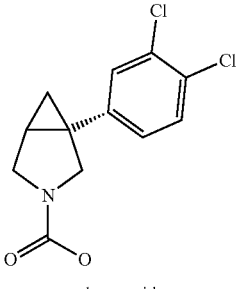<br>glucuronide | 447 | ~47.7<br>~51.4 |
| Lactam Compound 2 | 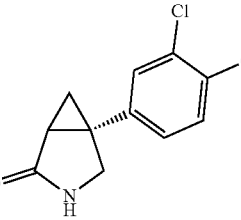 | 241 | ~49.3 |

One of the prominent metabolites is due to the oxidation of a carbon atom adjacent to the azabicyclo nitrogen to form the lactam (Compound 2) and accounted for about 63% of the metabolites formed (data not shown).

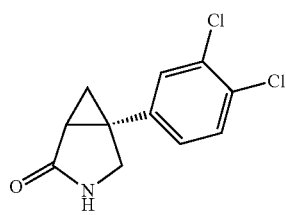

Compound 2

There is no appreciable formation of lactam isomer on the 5 position of the azabicyclo ring (data not shown). Another metabolite is due to the addition of $CO_2$ to the nitrogen to form a carbamate analog, which is subsequently conjugated to the glucuronide (Table 6). The addition of $CO_2$ to amines to form carbamates has been reported previously. The other two metabolites (labeled M02 and M03) have a molecular weight of 396, are minor in quantity, and their structures are not determined.

Example 5

NADPH-Dependent Lactam Formation Assessment

The effect of NADPH on lactam formation ((1S,5R)-5-(3,4-dichlorophenyl)-3-azabicyclo[3.1.0]hexan-2-one hydrochloride, Compound 2) is conducted by XenoBiotic Laboratories, Inc. (Plainsboro, N.J.). Amitifadine (10 μM) is incubated in pooled human male liver microsomes (0.25 mg/ml protein) for 30 minutes in the presence or absence of NADPH (1 mM). Bicifadine ((±)-1-(4-methylphenyl)-3-azabicyclo-[3.1.0]hexane HCl) (10 μM) is used as a positive control and the formation of the lactam metabolite of bicifadine (designated M12) is also monitored. Negative controls are determined by incubation of amitifadine and bicifadine in the absence of liver enzymes. The samples are analyzed using LC-MS/MS.

The system controller for the HPLC system is a Shimadzu SCL-10Avp, the pump model is a Shimadzu LC-10Avp, and the autosampler model is Shimadzu HTA. The analytical column is Phenomenex Luna C18 5 μm 50×2.0 mm which is set at room temperature and the autosampler is also at room temperature. The injection volume is 5 μl. Mobile phase A is 0.05% formic acid in water and mobile phase B is 0.05% formic acid in acetonitrile. The flow rate is 0.7 ml/minute and run time is 5 minutes. The gradient table is shown in Table 7. The mass spectrometer is an AB MDX Sciex API-4000 run in the turbo ion spray (ESI) positive ion detection mode and the scan mode is multiple reaction monitoring (MRM). The optimized mass spectrometry conditions are ion spray at 5000 V, curtain gas 10 units temperature 500° C., entrance potential 10 V, collision gas 6 units, and gas 1 and 2 each 50 units. The precursor ion, product ion, collision energy (CE), and declustering potential (DP) are shown in Table 8.

TABLE 7

Gradient table for study on lactam formation

| Time | Initial | 0.50 | 0.7 | 2.5 | 3.6 | 4.0 | 4.6 | 4.7 | 5.0 |
|------|---------|------|-----|-----|-----|-----|-----|-----|-----|
| % B  | 0       | 3    | 10  | 30  | 50  | 95  | 95  | 3   | 3   |

TABLE 8

Precursor ion, product ion, collision energy (CE), and declustering potential (DP)

| Compound | Precursor ion (m/z) | Product ion (m/z) | CE (eV) | DP (V) |
|----------|---------------------|-------------------|---------|--------|
| Amitifadine | 228 | 187 | 25 | 60 |
| Bicifadine | 174 | 133 | 25 | 60 |
| Compound 2 | 242 | 159 | 25 | 70 |
| M-12 | 188 | 105 | 25 | 80 |
| Bicifadine-d5 | 179 | 133 | 25 | 70 |
| Benzydamine | 310 | 86 | 28 | 60 |
| Benzydamine N-oxide | 326 | 102 | 25 | 60 |

To determine if the formation of the lactam metabolite (Compound 2) is catalyzed by NADPH-dependent enzymes, amitifadine (10 μM) is incubated in pooled human male liver microsomes for 30 minutes in the presence or absence of NADPH (1 mM). A compound with similar structure, bicifadine (10 μM), known to be metabolized by monoamine oxidase (MAO)-B to form the lactam metabolite (M12), is used as a control. The formation of Compound 2 from amitifadine is found to be partially NADPH-dependent with the quantity of Compound 2 formed in the presence of NADPH being 2 fold higher than that in the absence of NADPH (Table 9). There is no difference in the formation of M12 from bicifadine in the presence or absence of NADPH.

Example 6

Flavin Monooxygenases (FMO)-Dependent Lactam Formation Screening

FMOs, but not CYP enzymes, are sensitive to elevated incubation temperature. Thus, to determine if the formation of the lactam metabolite is mediated by FMOs and/or CYPs, the effect of pre-incubation temperature on the lactam formation is conducted by XenoBiotic Laboratories, Inc. (Plainsboro, N.J.). Amitifadine and bicifadine each at 10 μM concentrations are incubated in human liver microsomes which are previously pre-incubated at 37° C. or 45° C. for 5 minutes in the presence of NADPH. The incubation of benzydamine (positive control, 200 μM) is carried out concurrently. The samples are analyzed using LC-MS/MS (see NADPH-dependent lactam formation methodology).

The activity of flavin monooxygenases (FMOs) is decreased by elevated incubation temperature, whereas CYPs activity is not altered by elevated pre-incubation temperature. Thus, this technique can be used to determine if the oxidative reaction is catalyzed by FMOs or CYPs. A 5 minute pre-incubation at 45° C. did not alter the formation of Compound 2, indicating that rather than FMOs, CYPs may be the responsible enzymes for the formation of Compound 2 (Table 9). The formation of benzydamine N-oxide from benzydamine, a substance known to be oxidized by FMOs, is dependent on pre-incubation temperature with 4.6 fold more benzydamine N-oxide formed after the 37° C. pre-incubation than after the 45° C. pre-incubation. These data indicate that FMO is in large part deactivated by elevated pre-incubation temperature.

TABLE 9

Formation of the lactam metabolite Compound 2 in human liver microsomes from amitifadine, M12 from bicifadine, and benzydamine N-oxide from benzydamine

| NADPH conc., mM, temperature ° C. | Compound 2 | M12 | Benzydamine N-oxide |
|---|---|---|---|
| 0 mM at 37° C. | 0.04 ± 0.00 | 0.35 ± 0.02 | — |
| 1 mM at 37° C. | 0.08 ± 0.01 | 0.39 ± 0.02 | — |
| 1 mM at 37° C. | 0.05 ± 0.01 | 0.50 ± 0.02 | 35.70 ± 0.86 |
| 1 mM at 45° C. | 0.06 ± 0.01 | 0.51 ± 0.01 | 7.68 ± 1.51 |

The numbers are the mean ± standard deviation of the area under the curve ratio of analyte to the internal standard bicifadine-d5 chromatograph. No metabolites are detected in negative control samples.

Example 7

Monoamine Oxidase (MAO) Phenotyping

A study on the role of monoamine oxidases involved in the formation of the lactam metabolite is conducted by XenoBiotic Laboratories, Inc. (Plainsboro, N.J.). Incubations of amitifadine and bicifadine at 1 µM in human liver microsomes and human liver mitochondria suspensions in the absence or presence of various concentrations of MAO-A (clorgyline) and MAO-B (selegiline) inhibitors are performed. In addition, amitifadine and bicifadine are incubated with recombinant human MAO enzymes individually. The formation of Compound 2 and M12 in the incubation systems is monitored using LC-MS/MS methodology (see NADPH-dependent lactam formation methodology).

Figure 7:
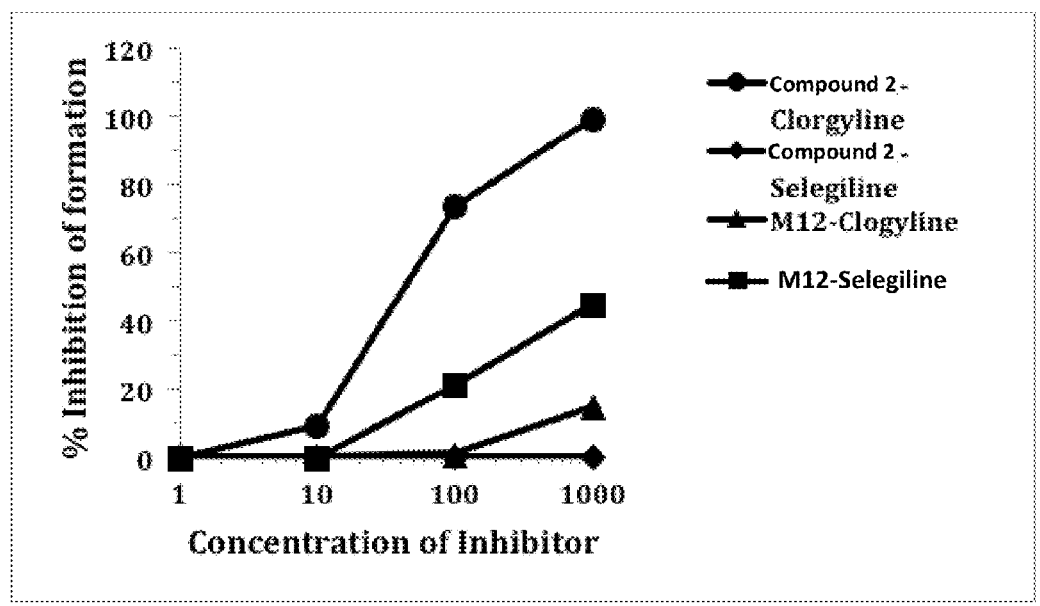
FIG. 7 is the inhibition of Compound 2 and M12 formation in human mitochondria by the MAO-A inhibitor clorgyline and MAO-B inhibitor selegiline. The formation of the lactam metabolites from 1 µM drug concentration is determined using a LC-MS/MS method after incubation at 37° C. for 30 minutes.

Amitifadine (1 µM) is incubated for 30 minutes at 37° C. with human liver mitochondria in the absence and presence of different concentrations of MAO inhibitors and the samples are analyzed by LC-MS/MS. The formation of Compound 2 from amitifadine is concentration-dependently decreased in the presence of the MAO-A inhibitor clorgyline, while the MAO-B inhibitor selegiline did not have an effect on Compound 2 formation (FIG. 7). The formation of M12 from bicifadine is inhibited by selegiline, but not markedly by clorgyline. Similar results are obtained using human liver microsomes preparations (data not shown). Incubation of amitifadine in the presence of human recombinant MAO-A enzyme resulted in Compound 2 formation at the rate of 7.0±2.7 pmol/min/mg protein, but no detectable Compound 2 is formed in the presence of human recombinant MAO-B enzyme.

Example 8

Inhibition of Human CYP Activity in Microsomes

The inhibitory potential of amitifadine towards seven human liver microsomal CYP activities is evaluated by Merck Research Laboratories (West Point, Pa.). Enzyme activities studied are CYP1A2-dependent phenacetin O-deethylation, CYP2B6-dependent bupropion hydroxylation, CYP2C8-dependent taxol 6α-hydroxylation, CYP2C9-dependent diclofenac 4'-hydroxylation, CYP2C19-dependent (S)-mephenyloin 4'-hydroxylation, CYP2D6-dependent bufuralol 1'-hydroxylation, and CYP3A4-dependent testosterone 6β-hydroxylation. The human liver microsomes are purchased from Tissue Transformation Technologies (Exton, Pa.) and from BD Biosciences (San Jose, Calif.) and are pooled from 10 individual samples.

To determine the CYP inhibitory potential, amitifadine at varying concentrations (0.05-100 µM) is incubated with liver microsomes in the presence of a single concentration of the enzyme substrate (approaching established $K_m$ value). The substrates are phenactin, bupropion, taxol, diclofenac, (S)-mephenyloin, bufuralol, and testosterone for CYP 1A2, 2B6, 2C8, 2C9, 2C19, 2D6, and 3A4, respectively. The positive control inhibitors are fluvoxamine (0.005-10 µM), N-(α-methylbenzyl)-1-aminobenzotriazole (0.005-10 µM), quercetin (0.02-50 µM), sulfaphenazole (0.005-10 µM), (R)—N-3-benzylphenobarbital (0.005-10 µM), quinidine (0.005-10 µM), and ketoconazole (0.005-10 µM), respectively. The incubation mixtures (0.2 ml final volume) contain microsomal protein (0.25 or 0.5 mg/ml) and 100 mM potassium phosphate buffer (pH 7.4). The reaction is initiated by the addition of NADPH, and is allowed to proceed for 10 to 30 min at 37° C. in a shaking water bath. The reactions are terminated with the addition of two volumes of acetonitrile containing an appropriate internal standard, and the samples are mixed and centrifuged. Aliquots of the supernatant are analyzed with a LC-MS/MS method. All incubations are run in duplicate and the enzyme activity in the absence of amitifadine and positive control inhibitors is assigned as control value (100%).

The LC-MS/MS analysis used is a Perkin Elmer HPLC system, comprised of a series 200 LC pump and autosampler. The mass spectrometer unit is a API Triple Quadrupole LC-MS/MS Mass Spectrometer (Sciex API 2000) with a APCI ion source. Mobile Phase A (CYP1A2) consists of solvent A: 0.05% formic acid in water, and solvent B: 0.05% formic acid in acetonitrile. Mobile Phase B (CYP2C9, CYP2C19, CYP2D6, CYP3A4, CYP2C8, and CYP2B6) consists of solvent A: 90/10 water/methanol with 0.05% formic acid, and solvent B: 10/90 water/acetonitrile with 0.05% formic acid.

Table 10 shows the HPLC and mass spectrometry analysis parameters for in vitro human CYP inhibition.

TABLE 10

HPLC and mass spectrometry analysis parameters for in vitro human CYP inhibition

| Enzymatic action (CYP) | HPLC column | Flow rate (ml/min) | Gradient | Metabolite Q1/Q3 mass ("m/z")* | Internal standard Q1/Q3 mass ("m/z")* |
|---|---|---|---|---|---|
| Phenacetin O-deethylation (CYP1A2) | AquaSep, 5 µm, 2.0 × 50 mm | 1.5 | 5 to 50 % B 1.4 min linear | Acetaminophen 151.9/110.1 | 4-OH-Butyranilide 180.2/71.0 |
| Diclofenac 4'hydroxylation (CYP2C9) | BDS Hypersil C8, 5 µm, 2 × 50 mm | 1.5 | 10 to70% B 1.9 min linear | 4'OH-Diclofenac 312/231.1 | Flufenamic acid 272.1/264.1 |

TABLE 10-continued

HPLC and mass spectrometry analysis parameters for in vitro human CYP inhibition

| Enzymatic action (CYP) | HPLC column | Flow rate (ml/min) | Gradient | Metabolite Q1/Q3 mass ("m/z")* | Internal standard Q1/Q3 mass ("m/z")* |
|---|---|---|---|---|---|
| (S)-Mephenytoin 4-hyroxylation (CYP2C19) | Zorbax SB-Aq, 5 μm, 4.6 × 50 mm | 1.5 | 20 to 80% B 1.9 min linear | 4'OH-Mephytoin 235.1/150.1 | Phenytoin 253.2/182.2 |
| Bufurarol 1'hydroxylation (CYP2D6) | BDS Hypersil C8, 5 μm, 2 × 50 mm | 1.5 | 0 to 50% B 1.9 min linear | 1'OH-Bufurarol 278.1/186.1 | DL-Propanolol 260.2/155.1 |
| Testosterone 6β-hydroxylation (CYP3A4) | BDS Hypersil C8, 5 μm, 2 × 50 mm | 1.5 | 0 to 50% B 1.9 min linear | 6β-OH-Testosterone 305.5/269 | Cortisone 361.0/163.2 |
| Taxol 6α-hydroxylation (CYP2C8) | Zorbax 300Extend C18, 5 μm, 4.6 × 50 mm | 1.5 | 20 to 80% B 2.0 min linear | 6α-OH-taxol 870.3/525.2 | Baccatin 587.2/405.2 |
| Bupropion hydroxylation (CYP2B6) | BDS Hypersil C8, 5 μm, 2 × 50 mm | 1.5 | 20 to 80% B 2.0 min linear | OH-Bupropion 256.2/184.2 | DL-Propanolol 260.2/155.1 |

The direct inhibitory potential of amitifadine (0.05-100 μM) for the seven human CYP activities is evaluated in human liver microsomes. Enzyme activities studied are CYP 1A2, 2B6, 2C8, 2C9, 2C19, 2D6, and 3A4. In comparison to the positive control inhibitors in the instances where amitifadine has measurable activity, it is 19 to 198 times less potent than comparator inhibitors (Table 11). According to the ranking convention, amitifadine is considered a potent inhibitor of CYP2B6 activity ($IC_{50}$=1.8 μM), a moderate inhibitor of CYP 1A2, 2C19, 2D6, 2C9, 3A4 activities ($IC_{50}$=10-22 μM), and a weak inhibitor of CYP2C8 activity ($IC_{50}$>100 μM) in human liver microsomes.

TABLE 11

Inhibition of CYP isoforms in pooled human liver microsomes by amitifadine and comparators.

| CYP isoform | Reaction | Compound | $IC_{50}$, μM (ratio Comparator/amitifadine) |
|---|---|---|---|
| CYP1A2 | Phenacetin O-deethylation | Fluvoxamine | 0.5 |
| | | Amitifadine | 9.5 (19) |
| CYP2B6 | Bupropion hydroxylation | N-(α-methylbenzyl)-1-AB[1] | 0.06 |
| | | Amitifadine | 1.8 (30) |
| CYP2C8 | Taxol 6α-hydroxylation | Quercetin | 18.7 |
| | | Amitifadine | >100 (>5.3) |
| CYP2C9 | Diclofenac 4'hydroxylation | Sulfaphenazole | 0.7 |
| | | Amitifadine | 22.6 (32) |
| CYP2C19 | (S)-Mephenytoin 4'-hydroxylation | (R)-N-3-benzyl-Phenobarb-ital | 0.3 |
| | | Amitifadine | 21.6 (72) |
| CYP2D6 | Bufuralol 1'-hydroxylation | Quinidine | 0.1 |
| | | Amitifadine | 19.8 (198) |
| CYP3A4 | Testosterone 6β-hydroxylation | Ketoconazole | 0.02 |
| | | Amitifadine | 15.5 (77) |

Amitifadine (0.05 to 100 μM) or comparators are incubated for 10 to 30 min at 37° C. and the formation of respective metabolite is determined by LC-MS/MS techniques.
[1] abbreviation for N-(α-methylbenzyl)-1-aminobenzatriazole.

Example 9

Determination of Brain and Plasma Levels of Amitifadine and Lactam Metabolite Compound 2 in Rat Brain and plasma levels of amitifadine are determined by Mithridion Inc. (Madison, Wis.). Adult male Sprague-Dawley rats weighing 229-291 g are obtained from Charles River Laboratories and acclimated for one week under standard housing conditions prior to use. The studies are conducted in accordance with the Institutional Animal Care and Use Committee guidelines. Rats in groups of three are food-deprived 16 hours prior to the oral administration of drug or vehicle (distilled water) with a dosing volume of 1 ml/kg. Amitifadine solution (10 mg/ml) in distilled water is freshly prepared on the day of dosing and administered to rats at 10 mg/kg. At 0.5, 1, 2, and 4 hour after dosage, animals are briefly anesthetized in a chamber containing 4% isoflurane and rapidly decapitated. Trunk blood is collected in heparinized tubes (9 units/ml whole blood), immediately chilled to 4° C., centrifuged, and the plasma is frozen at −80° C. until analyzed. Brains are quickly removed, bisected along the midline, and frozen at −80° C. until analyzed.

Plasma and brain samples are allowed to thaw on ice and are homogenized in a 20 ml glass vial in two volumes of ice cold water using a handheld homogenizer (VDI 12, VWR International). Standard curves are prepared in water, control plasma, and control brain homogenate. Equal volumes (100 µl) of plasma or brain homogenate samples, distilled water and internal standard are mixed in 1.5 ml polypropylene tubes and 300 µl of acetonitrile is added to each mixture. Samples are then mixed thoroughly by placing on a shaker at 200 RPM for 40 minutes at room temperature. The samples are then centrifuged at 10,000×g for 10 minutes at 4° C. and the supernatant (200 µl) is transferred to a tube containing 2 µl of 10% formic acid. The samples are subjected to a Zorbax SBC18 Solvent Saver Plus 3.0×150 mm 3.5-µm column on a Shimadzu Prominence LC. The compounds are eluted at 0.6 ml/min flow rate using a gradient of 40% to 100% mobile phase B in mobile phase A. Mobile phase A consists of water with 10 mM ammonium formate and 0.065% formic acid; and mobile phase B consists of 90% methanol with 10 mM ammonium formate and 0.065% formic acid. The concentration of compound in the column effluent is measured using an Applied Biosystems API-3200 triple quadrupole mass spectrometer.

Table 12 provides mass spectrometry conditions.

TABLE 12

Mass spectrometry conditions

|  | Amitifadine | Compound 2 |
| --- | --- | --- |
| Parent > daughter (m/z) | 228.0 > 187.0 | 242.0 > 158.9 |
| Probe Temperature(° C.) | 400 | 400 |
| Ion Source Voltage (V) | 5500 | 5500 |
| Ion Source Gas 1 (psi) | 50 | 50 |
| Ion Source Gas 2 (psi) | 60 | 60 |
| Curtain Gas (psi) | 25 | 25 |
| Collision Gas (psi) | 5 | 5 |
| Declustering Potential (V) | 46 | 56 |
| Entrance Potential (V) | 9.5 | 10.5 |
| Collision Energy (V) | 31 | 35 |
| Collision Cell Exit Potential (V) | 4 | 4 |

Figure 8:
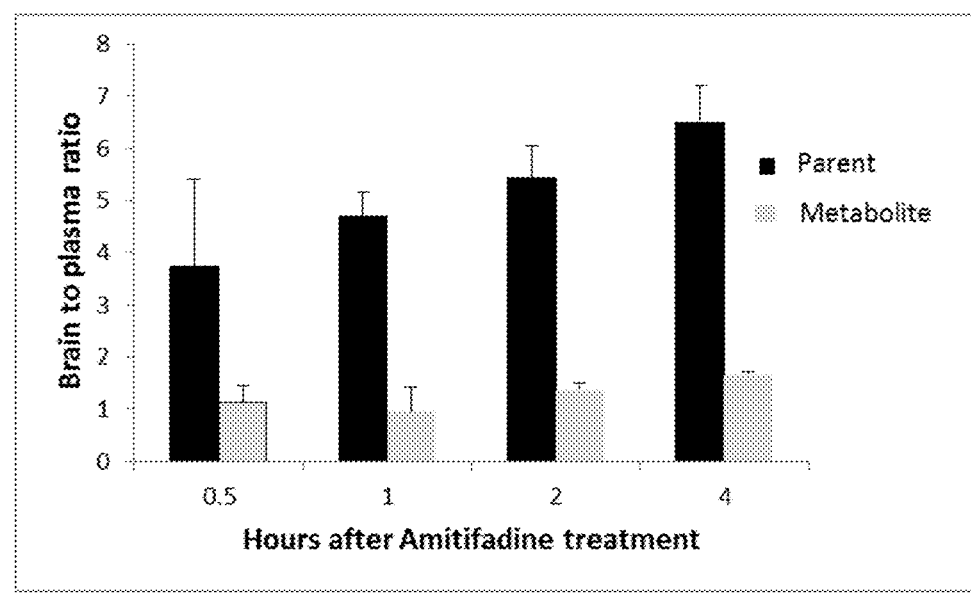
FIG. 8 shows the brain to plasma ratio of amitifadine (parent) and Compound 2 (metabolite) determined in rats at various time points. Amitifadine is administered orally at 10 mg/kg po., and concentrations of amitifadine and Compound 2 are determined by a LC-MS/MS method. The mean±SEM plasma levels of amitifadine are 830±360, 570±100, 798±334, and 1233±98 at 0.5, 1, 2 and 4 hours, respectively, and the plasma levels of Compound 2 are 1153±610, 1620±303, 3831±1127, and 8896±794, respectively.

After oral administration of amitifadine (10 mg/kg) to rats, the concentrations of amitifadine and Compound 2 in rat brain (µg/g) and plasma (µg/ml) are determined by LC-MS/MS. The brain to plasma ratio for amitifadine is 3.7, 4.7, 5.4, and 6.5, at 0.5, 1, 2 and 4 hours after oral administration, respectively, indicating preferential penetration into the brain (FIG. 8). The brain to plasma ratio for Compound 2 is 1.1, 1.3, 1.4, and 1.7, respectively. Recovery for amitifadine is 128% in plasma and 67% in brain homogenate, and recovery of the lactam metabolite Compound 2 is 107% in plasma and 105% in brain.

The above examples show the characteristics of amitifadine including human plasma protein binding, membrane permeability, metabolic stability in human hepatocytes, routes of in vitro metabolism in human tissues, and rat brain penetration. Amitifadine is bound to human plasma protein with 99.4% of the drug plasma protein bound, possibly due to its lipophilic nature. Similar binding at 1 and 10 µM concentrations indicate no increase in free concentration with the increase in drug concentrations. In the Caco-2 human intestinal cell model of intestinal barrier, amitifadine (10 µM) shows permeability in both absorptive and secretory directions. However, in the absorptive direction there is a loss in mass balance (62% recovery), which contributes to the lower permeability in the absorptive direction. It is not clear what contributes to the decreased recovery, but significant deviations from 100% recovery may be due to solute adsorption to the apparatus or monolayer, or chemical or metabolic instability during the course of the experiment. Amitifadine may have little propensity for active secretion.

Because amitifadine is permeable and soluble, the oral absorption is not likely to be a rate-limiting step and, thus, the oral bioavailability is unlikely to be affected by other co-administered drugs.

The metabolic stability of amitifadine is measured in human hepatocytes and the results indicate that it is metabolized to a modest extent with 82.4% of the parent drug remaining after 4 hours incubation. The major metabolite, accounting for about 60% of the metabolism, is due to oxidation of a carbon atom adjacent to the azabicyclic nitrogen to form the lactam analog Compound 2. Another relatively prominent metabolite formed is due to the addition of $CO_2$ to the nitrogen to form a carbamate analog, which is subsequently conjugated to the glucuronide.

The prominent formation of the lactam metabolite Compound 2 of amitifadine is further investigated to determine the responsible enzymes. Incubation of amitifadine with human liver microsomes in the presence of NADPH doubles the formation of Compound 2, indicating in part formation from NADPH-dependent enzymes such as CYP and FMO. The lack of pre-incubation temperature-sensitivity rules out formation of the lactam by FMOs and indicates that Compound 2 forms at least in part by CYPs. The NADPH-independent metabolism pathway is investigated by studying the effect of MAO inhibitors on the formation of Compound 2 using human liver microsomes. Surprisingly, in contrast to the metabolism of a structurally similar azabicyclo compound, bicifadine, which is metabolized to a lactam exclusively by MAO-B, MAO-A is found to metabolize amitifadine to the lactam Compound 2. The formation of Compound 2 is blocked by an MAO-A inhibitor, whereas the MAO-B inhibitor did not alter Compound 2 formation. Further, Compound 2 is formed by incubation with recombinant human MAO-A enzyme, but not recombinant human MAO-B enzyme. Metabolism by multiple routes is a desired property for a drug because it offers alternative metabolic pathways if one or more pathways are altered by drug-induced inhibition or a polymorphic change such as found with CYP 2D6 and 2C19 isoforms.

Amitifadine has relatively low inhibition ($IC_{50}$ values of >10 µM) for the four major drug metabolizing CYPs, i.e. CYP 2D6, 2C9, 2C19 and 3A4, and stronger inhibition on CYP2B6, which is involved in less than 10% of metabolism of marketed drugs. Amitifadine has considerably lower affinity for the CYP isoforms than the positive comparators. Amitifadine requires a dosage of at least 50 mg in humans to have a sufficient concentration at plasma $C_{max}$ to inhibit CYP2B6 activity by 50%. The other CYP isoforms studied required doses of amitifadine greater than 300 mg to have $C_{maxs}$ equivalent to the respective concentrations required to produce 50% inhibition.

Amitifadine is plasma protein bound, permeable, and partitions favorably into the brain versus plasma. Amitifadine is metabolized relatively slowly by human hepatocytes and the major metabolite is the lactam Compound 2. Compound 2 has low affinity for monoamine transporters and is formed by multiple enzymes—MAO-A and possibly one or more CYP enzymes. Amitifadine is a weak/moderate inhibitor of CYP 2D6, 3A4, 2C9, and 2C19, and with the low concentration of free drug in plasma, it is possible that CYP inhibition caused by amitifadine is low.

Although the foregoing has been described in detail by way of example for purposes of clarity of understanding, persons of ordinary skill in the art will understand that certain changes and modifications may be practiced within the scope of the appended claims which are presented by way of illustration not limitation. In this context, this disclosure is not limited to the particular formulations, processes, and materials disclosed herein, as such formulations, process steps, and materials may vary somewhat. Also, the terminology employed herein is used for describing particular embodiments only, and is not intended to be limiting of this disclosure embodied in the claims. Various publications and other reference information have been cited within the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

What is claimed is:

1. A method of treating pain comprising administering to a human in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the human is a heavy drinker.

2. A method of treating pain comprising administering to a patient in need thereof an effective amount of (1R,5S)-(+)-1-(3,4-dichlorophenyl)-3-azabicyclo[3.1.0]hexane, in free and/or pharmaceutically acceptable salt form, substantially free of the corresponding (−) enantiomer, wherein the patient has compromised liver function.

3. The method according to claim 1, wherein the effective amount of (1R,5S)-(+)-1-(3,4-dichlorophenyl)-3-azabicyclo[3.1.0]hexane, in free and/or pharmaceutically acceptable salt form, comprises less than or equal to 2% w/w of the corresponding (−) enantiomer.

4. The method according to claim 1, wherein the effective amount of (1R,5S)-(+)-1-(3,4-dichlorophenyl)-3-azabicyclo[3.1.0]hexane, in free and/or pharmaceutically acceptable salt form, comprises less than or equal to 1% w/w of the corresponding (−) enantiomer.

5. The method according to claim 1, wherein the (1R,5S)-(+)-1-(3,4-dichlorophenyl)-3-azabicyclo[3.1.0]hexane is in pharmaceutically acceptable salt form.

6. The method according to claim 1, wherein the (1R,5S)-(+)-1-(3,4-dichlorophenyl)-3-azabicyclo[3.1.0]hexane in pharmaceutically acceptable salt form is (1R,5S)-(+)-1-(3,4-dichlorophenyl)-3-azabicyclo[3.1.0]hexane hydrochloride.

7. The method according to claim 1, wherein the (1R,5S)-(+)-1-(3,4-dichlorophenyl)-3-azabicyclo[3.1.0]hexane, in free and/or pharmaceutically acceptable salt form, is Polymorph A substantially free of other polymorphic forms.

8. The method according claim 1, wherein the pain is chronic pain.

9. The method according to claim 1, wherein the pain is neuropathic pain.

10. The method according to claim 1 further comprising administering a second therapeutic agent.

11. A method of treating pain comprising concurrently or sequentially administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) acetaminophen.

12. A method of treating pain comprising concurrently or sequentially administering to a patient in need thereof an effective amount of: (a) (1R,5S)-(+)-1-(3,4-dichlorophenyl)-3-azabicyclo[3.1.0]hexane, in free and/or pharmaceutically acceptable salt form, and (b) a non-steroidal anti-inflammatory drug.

13. The method according to claim 11, wherein the effective amount of (1R,5S)-(+)-1-(3,4-dichlorophenyl)-3-azabicyclo[3.1.0]hexane, in free and/or pharmaceutically acceptable salt form, comprises less than or equal to 2% w/w of the corresponding (−) enantiomer.

14. The method according to claim 11, wherein the effective amount of (1R,5S)-(+)-1-(3,4-dichlorophenyl)-3-azabicyclo[3.1.0]hexane, in free and/or pharmaceutically acceptable salt form, comprises less than or equal to 1% w/w of the corresponding (−) enantiomer.

15. The method according to claim 11, wherein the (1R,5S)-(+)-1-(3,4-dichlorophenyl)-3-azabicyclo[3.1.0]hexane is in pharmaceutically acceptable salt form.

16. The method according to claim 11, wherein the (1R,5S)-(+)-1-(3,4-dichlorophenyl)-3-azabicyclo[3.1.0]hexane in pharmaceutically acceptable salt form is (1R,5S)-(+)-1-(3,4-dichlorophenyl)-3-azabicyclo[3.1.0]hexane hydrochloride.

17. The method according to claim 11, wherein the (1R,5S)-(+)-1-(3,4-dichlorophenyl)-3-azabicyclo[3.1.0]hexane, in free and/or pharmaceutically acceptable salt form, is Polymorph A substantially free of other polymorphic forms.

18. The method according to claim 11, wherein the pain is chronic pain.

19. The method according to claim 11, wherein the pain is neuropathic pain.

20. The method according to claim 11, wherein the patient is a heavy drinker.

21. The method according to claim 11, wherein the patient is a binge drinker.

22. The method according to claim 11, wherein the patient has compromised liver function.

23. The method according to claim 11, wherein the patient is a codeine non-responder.

* * * * *